US007285386B2

(12) United States Patent
Ozbun

(10) Patent No.: US 7,285,386 B2
(45) Date of Patent: Oct. 23, 2007

(54) RHPV AS A MODEL FOR HPV-INDUCED CANCERS

(75) Inventor: Michelle A. Ozbun, Albuquerque, NM (US)

(73) Assignee: University of New Mexico, and Educational Institution of the State of New Mexico, Albuquerque, NM (US)

( * ) Notice: Subject to any disclaimer, the term of this patent is extended or adjusted under 35 U.S.C. 154(b) by 384 days.

(21) Appl. No.: 10/978,239

(22) Filed: Oct. 29, 2004

(65) Prior Publication Data
US 2005/0144657 A1    Jun. 30, 2005

Related U.S. Application Data

(60) Provisional application No. 60/515,476, filed on Oct. 29, 2003.

(51) Int. Cl.
C12Q 1/68 (2006.01)
(52) U.S. Cl. .......................... 435/6; 435/325
(58) Field of Classification Search ............... 435/6, 435/325
See application file for complete search history.

(56) References Cited

U.S. PATENT DOCUMENTS

| | | | |
|---|---|---|---|
| 5,994,115 | A | 11/1999 | Meyers |
| 6,110,663 | A | 8/2000 | Meyers et al. |
| 6,399,353 | B1 | 6/2002 | Meyers et al. |
| 6,495,361 | B1 | 12/2002 | Hermonat et al. |
| 6,596,924 | B1 | 7/2003 | Jianmin |
| 6,797,491 | B2 | 9/2004 | Neefe et al. |

OTHER PUBLICATIONS

Chan et al. (Jul. 1997) "Genomic Diversity and Evolution of Papillomaviruses in Rhesus Monkeys," *J. Virol.* 71(7):4938-4943.
Debattista et al. (Jun. 2003) "Immunopathogenesis of *Chlamydia trachomatis* Infections in Women," *Fertility and Sterility* 79:1273-1287.
Howley, P.M. (1996) "*Papillomavirinae*: The Viruses and Their Replication," In; B.N. Fields et al. eds., *Fields Virology*, Third Edition, Second ed. Raven Press, New York, pp. 2045-2076.
Gillison et al. (May 2000) "Evidence for a Causal Association Between Human Papillomavirus and a Subset of Head and Neck Cancers," *J. Nat. Canc. Inst.* 92:709-720.
Kloster et al. (May 1988) "Molecular Cloning and Characterization of the DNA of two Papillomaviruses from Monkeys," *Virol.* 166:30-40.
Lin et al. (Sep. 2002) "Chaperone Proteins Abrogate Inhibition of the Human Papillomavirus (HPV) E1 Replicative Helicase by the HPV E2 Protein," *Mol. Cell Biol.* 22:6592-6604.

Liu et al. (Nov. 1998) "Human Hsp70 and Hsp40 Chaperone Proteins Facilitate Human Papillomavirus-11 E1 Protein Binding to the Origin and Stimulate Cell-free DNA Replication," *J. Biol. Chem.* 273(13):30704-30712.
Morozov et al. (1995) "HPV16 E7 Oncoprotein Induces Expression of a 110 kDa Heat Shock Protein," *FEBS Lett.* 371:214-218.
Myers et al. (Oct. 1997) "Synthesis of Infectious Human Papillomavirus Type 18 in Differentiating Epithelium Transfected with Viral DNA," *J. Virol.* 71(10):7381-7386.
Ostrow et al. (Oct. 1990) "A Rhesus Monkey Model for Sexual Transmission of a Papillomavirus Isolated from a Squamous Cell Carcinoma," *Proc. Natl. Acad. Sci. USA* 87:8170-8174.
Ostrow et al (1991) "Characterization of the Complete RhPV 1 Genomic Sequence and an Integration Locus from a Metastatic Tumor," *Virol.* 181:424-429.
Ozbun, M.A. (Nov. 2002) "Infectious Human Papillomavirus Type 31b: Purification and Infection of an Immortalized Human Keratinocyte Cell Line," *J. Gen. Virol.* 83:2753-2763.
Ozbun, M.A. (Nov. 2002) "Human Papillomavirus Type 31b Infection of Human Keratinocytes and the Onset of Early Transcription," *J. Virol.* 76:11291-11300.
Ozbun et al. (Apr. 1998) "Temporal Usage of Multiple Promoters During the Life Cycle of Human Papillomavirus Type 31b," *J. Virol.* 72:2715-2722.
Ozbun et al. (Apr. 1999) "Two Novel Promoters in the Upstream Regulatory Region of Human Papillomavirus Type 31b are Negatively Regulated by Epithelial Differentiation," *J. Virol.* 73:3505-3510.
Schilling et al. (May 1998) "A Novel Human DnaJ Protein, hTid-1, A Homolog of the Drosophila Tumor Suppressor Protein Tid56, Can Interact with the Human Papillomavirus Type 16 E7 Oncoprotein," *Virol.* 247:74-85.
Steele et al. (Aug. 2002) "Variable Expression of Some "Housekeeping" Genes During Human Keratinocyte Differentiation," *Anal. Biochem.* 307:341-347.
Sullivan et al. (May 2001) "The Virus-Chaperone Connection," *Virol.* 287:1-8.
Walboomers et al. (May 1999) "Human Papillomavirus is a Necessary Cause of Invasive Cervical Cancer Worldwide," *J. Pathol.* 189:12-19.
Wood, Charles E, et al., "Characterization and Experimental Transmission of an Oncogenic Papillomavirus in Female Macaques," Journal of Virology, (Jun. 2007) vol. 8, No. 12, pp. 6339-6345.

*Primary Examiner*—Ali R. Salimi
(74) *Attorney, Agent, or Firm*—Greenlee Winner and Sullivan, PC

(57) ABSTRACT

Provided is an animal model system for the study of papillomaviruses, especially anogenital papillomaviruses, especially those causing anogenital and/or head and neck cancers. The Rhesus papillomavirus (especially RhPV1) is a useful model for human papillomaviruses which cause anogenital infections and cancers of the anogenital region and/or the head, neck and respiratory system.

4 Claims, 6 Drawing Sheets at epithelial confluence, submerged monolayer is transferred to raft culture 2 weeks growth

```
                        SEQUENCE LISTING

<160> NUMBER OF SEQ ID NOS: 14

<210> SEQ ID NO 1
<211> LENGTH: 17
<212> TYPE: DNA
<213> ORGANISM: Artificial
<220> FEATURE:
<223> OTHER INFORMATION: Oligonucleotide useful as a primer.

<400> SEQUENCE: 1
aaggcaagcc atacggg                                                17

<210> SEQ ID NO 2
<211> LENGTH: 17
<212> TYPE: DNA
<213> ORGANISM: Artificial
<220> FEATURE:
```

-continued

<223> OTHER INFORMATION: Oligonucleotide useful as a primer.

<400> SEQUENCE: 2
ggcctaaacc taccctc                                                17

<210> SEQ ID NO 3
<211> LENGTH: 20
<212> TYPE: DNA
<213> ORGANISM: Artificial
<220> FEATURE:
<223> OTHER INFORMATION: Oligonucleotide useful as a primer.

<400> SEQUENCE: 3
gtctggcgtg ctgatgatgc                                             20

<210> SEQ ID NO 4
<211> LENGTH: 19
<212> TYPE: DNA
<213> ORGANISM: Artificial
<220> FEATURE:
<223> OTHER INFORMATION: Oligonucleotide useful as a primer.

<400> SEQUENCE: 4
agtagccacg aagagttac                                              19

<210> SEQ ID NO 5
<211> LENGTH: 20
<212> TYPE: DNA
<213> ORGANISM: Artificial
<220> FEATURE:
<223> OTHER INFORMATION: Oligonucleotide useful as a primer.

<400> SEQUENCE: 5
agtagccacg aagagttacg                                             20

<210> SEQ ID NO 6
<211> LENGTH: 22
<212> TYPE: DNA
<213> ORGANISM: Artificial
<220> FEATURE:
<223> OTHER INFORMATION: Oligonucleotide useful as a primer.

<400> SEQUENCE: 6
caagtgcttc catcattttc cg                                          22

<210> SEQ ID NO 7
<211> LENGTH: 18
<212> TYPE: DNA
<213> ORGANISM: Artificial
<220> FEATURE:
<223> OTHER INFORMATION: Oligonucleotide useful as a primer.

<400> SEQUENCE: 7
cacctgagtc tgaccgac                                               18

<210> SEQ ID NO 8
<211> LENGTH: 18
<212> TYPE: DNA
<213> ORGANISM: Artificial
<220> FEATURE:
<223> OTHER INFORMATION: Oligonucleotide useful as a primer.

<400> SEQUENCE: 8
cacaaaggac tgaccggc                                               18

```
<210> SEQ ID NO 9
<211> LENGTH: 24
<212> TYPE: DNA
<213> ORGANISM: Artificial
<220> FEATURE:
<223> OTHER INFORMATION: Oligonucleotide useful as a primer.

<400> SEQUENCE: 9
gctagtgcat atgtctatag gaac                                          24

<210> SEQ ID NO 10
<211> LENGTH: 20
<212> TYPE: DNA
<213> ORGANISM: Artificial
<220> FEATURE:
<223> OTHER INFORMATION: Oligonucleotide useful as a primer.

<400> SEQUENCE: 10
gatgacccag atcatgtttg                                               20

<210> SEQ ID NO 11
<211> LENGTH: 22
<212> TYPE: DNA
<213> ORGANISM: Artificial
<220> FEATURE:
<223> OTHER INFORMATION: Oligonucleotide useful as a primer.

<400> SEQUENCE: 11
aacaccccag ccatgtacgt tg                                            22

<210> SEQ ID NO 12
<211> LENGTH: 22
<212> TYPE: DNA
<213> ORGANISM: Artificial
<220> FEATURE:
<223> OTHER INFORMATION: Oligonucleotide useful as a primer.

<400> SEQUENCE: 12
actccatgcc caggaaggaa gg                                            22

<210> SEQ ID NO 13
<211> LENGTH: 21
<212> TYPE: DNA
<213> ORGANISM: Artificial
<220> FEATURE:
<223> OTHER INFORMATION: Oligonucleotide useful as a primer.

<400> SEQUENCE: 13
ggagcaatga tcttgatctt c                                             21

<210> SEQ ID NO 14
<211> LENGTH: 8026
<212> TYPE: DNA
<213> ORGANISM: Rhesus monkey papillomavirus type 1

<400> SEQUENCE: 14
tacttaacta tactcctgag tatgaaaaag ggtgtaaccg aaaacggtgc aaccgaaagc    60
ggtgcatata aaagctcct gaaactttgg ttttttgtgg caatggtaga ctgccctggc   120
gagccaaacg aattgcccag gaccattcac gaactatgcg agcagcgtga ggagaccctg   180
cacgagcttc aattggagtg cgtgtattgc ctgaaggaac taacacgcat tgaggtatat   240
gattttgcac ggtgggattt aagattggtg catagacaag gcaagccata cggggtatgt   300
cccatatgct tgaggtttta ctcaaaaatt cgaaaatata ggcgatacga gtattcaata   360
```

-continued

| | | |
|---|---|---|
| tatgggtgta ctttagagcg tagaactaga aaacagttag tggaggtatt aataaggtgt | 420 |
| tattgttgtc agaagcccct gtgtcccatt gaaaagcaaa gacacgtgga ccaaggacaa | 480 |
| aggttccaca gaatagcggg acagtggacc ggaaggtgct tgatgtgctg gagaccaaca | 540 |
| gtacctgaga cccagccaga cactgatcaa caggggcagta gtttcttgca agcatgattg | 600 |
| ggcctaaacc taccctcgag gacattgtcc tagatttgca accatttcca caaccgcaac | 660 |
| cggtcgacct tatgtgttat gagcaattat ctgacagctc agaggatgag gatgaagtag | 720 |
| accatcatca caataatcag cagcagcatc atcagcacgc cagacctgaa gtaccagagg | 780 |
| atggtgattg ttatagaatt gtgagcgatt gttacagctg tggcaagcca ctgaggctgg | 840 |
| ttgtggttag tagccacgaa gagttacgtg tgctagagga cctgctgatg ggcacgcttg | 900 |
| acattgtgtg tcccagctgt gccagcagag tgtaactgca atggaccctg aaggtacacc | 960 |
| agggggaaggg gtggggtgta cggggtggtt taatgtggag gctatagtag aacgtaaaac | 1020 |
| gggggatgtg tgtcagagg acgaagacga cacagaggat acaggataag atttggtaga | 1080 |
| ctttatagat gacacatgtg gaagtgtgca gacaggggac gaggcacctg ggcgttgtt | 1140 |
| gcacgcacag gaaacacaag cgcatgcaga ggcagtgcag gttttaaaac gaaagtttgt | 1200 |
| aggcagtccg gcagttagtc cgttgggaaa ctacaatccc tgtgtagaca gggatttaag | 1260 |
| tcccagatta aatgaaataa gtttaaacca aggcagcgga caggcaaaac ggagactgtt | 1320 |
| tttgccggac agcggttatg gcaatactga agtggaaacg tcgctattgc aggtagcagg | 1380 |
| gggggggcggc caggatgtac aggcaggggg aaggaaaac acacggccag atgacgggg | 1440 |
| ggggatgcc acgcagctgc tccgttgcag caacttaaaa gccactttgc tgagtaaatt | 1500 |
| taaatctgtg tatggagtta gcttttcaga gttggtgcga agcttaaaaa gcgacaggac | 1560 |
| cacgtgcgct gactgggtgg tgggggcagc gggggtccat catagcgtgg cagagggtt | 1620 |
| aaagcagctc attcagcctt tttgcagtta tgcacacatc cagtgcctta catgcgactg | 1680 |
| ggggtgtac ctgctactgc tggcacggtt taagtgtggc aaaaacagac taacagtttc | 1740 |
| taaatgcatg agcacgctgt taatgtgca agaaacgcac atgctaattg aaccaccgaa | 1800 |
| gctgcgtagc gcagcagcag ctctatactg gtacaggaca ggtatatcaa atgtaagtga | 1860 |
| agtaataggg gaaacacctg agtggattac aagacagaca atgtttcaac atggcctgga | 1920 |
| ggacagtata tttgatttgt ctgaaatggt gcagtgggca tacgaccacg actttacaga | 1980 |
| tgacagtgtg atagcgtacg agtatgcaca gctggcaggg atagacagca acgctgctgc | 2040 |
| attttttaaaa agtaatgcac aggccaaata tgtgaaggat tgtgccacta tgtgtaggca | 2100 |
| ctacaaaaga gccgaaaggc aacagatgac tatgtcacag tggataaaac aaaggtgtga | 2160 |
| aaaaactgat gatggagggg actggaggcc aatagtgcag ttttttaaggt accaagggt | 2220 |
| ggagtttata gcatttttag cagctttaaa gctgtttttg aagggcattc caaaaaaaaa | 2280 |
| ctgcatagtg ttatttggac cgccaaatac aggtaaatcc tactttggca tgagcttaat | 2340 |
| acatttcttg caagggtcta tcatttcata tgtaaattcc aacagtcact tttggttgca | 2400 |
| gcctctggca gatgctaagg tggccatgtt ggatgatgca actcctcagt gctggtccta | 2460 |
| tatagataat tatttaagga acgcactgga cgggaacccc attagtgttg atagaaaaca | 2520 |
| taaaaatctt gtacagatga agtgccccc attgcttatt acctcaaaca ccaatgcagg | 2580 |
| tcaggatgac aggtggatgt atttgcacag tagaatggtt gtgtttacat tgaacagcc | 2640 |
| atttccattt gatcagaacg gtaatccagt ttatgagtta aatgataaaa actggaaatc | 2700 |
| cttttttctca aggacatggt ccagattaga tttacaagag gaagaggaga cggaaaatga | 2760 |

```
tggaagcact tgcagagcgt ttaagtgcgt tgcaggacag aatcttagaa ctgtatgaag    2820
ctgatagcaa ggacttaaaa gaccaaatag agcactggaa atgtgtgcgc caagaatgtg    2880
cagtgttgta taaggcacgg gaagtagggt tttcccacct gaaccatcag gtggtgccat    2940
cattaactgt gtcacgggct aaagcccaca agcaattga agtgcagctg cattagaga     3000 gtttacaaaa ttcggagtat aacaatgagg agtggacgct gcaagatgcc agcttggaga    3060
tgtggcacac agaacctaag ggatgcttca aaaaacagg tgttccagta acagttttgt     3120
ttgactgtga caaagacaat accatggagt atgtgctgtg gggacacata tatgtgtggg    3180
gggacaatgg atgggtgaag acattcggtg aggcggacaa ctggggtctg cactataccg    3240
ttgctgggga aaaggtgtac tatgtgcagt tttatgagga tgctaaaaaa tatggacatg    3300
gaaatggaaa tggagatggc tatgagtggg aggtgcatgt tggtgggacg gtaatgcatt    3360
attctgactc tgtgtctagc gctacccact gcgacaaact acccactgtt gaaattgtta    3420
gcggactgca acacatcaac ccatcacccc ccccgccaa cccagcgcc aaggaaaacg      3480 tgtggtcatc gcctgcaaag cgagtgcgtc ggtcagactc aggtggagat ccagtgcggg    3540
ccttggacgg taaaagccgg tcagtccttt gtggatctgc acacaacaac gctacaggga    3600
gttccggtga cagtgactat acgcctatag tgcacctaaa aggtgaatct aactgtttga    3660
agtgtttgcg gttcagactg ggaaagcata agcacctgta tattaatata tcgtccacct    3720
ggaggtgggc aaaccatgca agtgagaaag caattgtaac tgtgacattt gcaaatgagc    3780
ttcaaagaca acagtttttta aacactgtaa aaataccttc tactgtaact ctgtcacaag    3840
gagtaatgac tgtgtagtgt gcattggcac acagggtttt gtatttttt ttttacaagt     3900 actgtttgta attaattttg tatattgact gtatattgaa ttgtggtgtg cattggcaca    3960
cagtggtctc atttcaagcc tgtacataca ttgaacagta tccaggtact gtgtaaagcc    4020
aattgttgct gctacgcttg taaccgcca ccattctgct gtttctggtt gtgttttttgc    4080 tgctgttttt gcttggcctt gtgttttgtg cacttgttga tcgctgcttt ctgtgttttt    4140
ccggtatgcc tcagtgttgc tgcttatgct gttgttctgg gtgtccatag tgaacccgtt    4200
tgcagctttt ggtctgtgtt tgttttgttt tttaaccccg ttgcttttga tacacctgca    4260
tgccctcagt gtggtttaca gcagaatgat gtaaatactg cacatagaca tgttattatc    4320
agttattttg ctattgttgc tgttaatatt tactttgttt tggcactact tgttggtgct    4380
gcgtttaaag ccaccagcag ggcgcgcacg taaatgtaaa cagctgagac ggcggcgcag    4440
ataataaacg tcacacaata aagcgtcatg aagcatgcac acttgtcgcg gcgcaagcga    4500
gcagccccgc gcccacctgg tgggcggcaa aagcgtgcat ctgccacgca gctgtaccaa    4560
acctgcaagg cggcaggcac atgcccccc gatgttatcc ctaaggtgga aggcacaacc     4620
gtagcagatc aaattttaaa gtatggcagc atgggtgtat actttggggg tttgggcatt    4680
ggctctggtg ctggcacggg cggaagaagc ggctacgtgc ccctaggttc acgtcccgca    4740
tccattcccg agccgttgcc acgaccacca gtaacaattg agcctgtggg cccttccgat    4800
ccctccattg tgtcattgct ggaagagtcc agactaatag aggcaggtgt tccagccccc    4860
acattcccca ctcatggggg gtttgaaatt agcacatctg aagttagcac acccgctgtc    4920
ctggatgtgt ctagcggtgg ctctgatgtg cacgttagtg tgacctcctt tacaaaccct    4980
acctttactg agccatctgt gctgcgaccc ccgcccccg tagaggcgtc tggacgcctg     5040
gtaatctctg catcctctgt cagcacgcat agctacgaag aaatacccat ggacacattt    5100
```

-continued

```
gtaataactg gagaccacaa ctataacaca accagcacac ccattcctgg ttcacgtgcc    5160
cctgcacgac ttggtctata tggacgtgct acccagcaag tgcgggtggt ggatcctgca    5220
tttataacca ccccctgcgcg actggtgaca tatgacaacc ctgcatatga gggtgtggac    5280
gatgccaccc tgcaattttc ccactctgac attcaccagc cgccagatcc tgacttcctt    5340
gacattgtgg cattgcacag gcccgccttg acctcacgta agggcaccgt gcgctttagc    5400
cgattaggcc agcgggcaac actaaccacg cgcagtggta agcgtattgg ggccaaggtg    5460
catttctatc atgacctcag tcccattgcc cctgcagaaa gcatcgagtt gcagcccctg    5520
tcatctcagg gagagctgta tgacatatat gcagatgtag acgggcaaga ggacgctgca    5580
gctgtggcta cacccccatt aaacagcaac agcagtggca ttgcaagccc ctggaacacc    5640
acagtgccac tcagtgcagg gcggacgtg acgctgcagt ccggccccga cgtgtccctg    5700
gatgcaccag tggctgaatc gcctgtgcac cctggagtgc ctctaaggcc ttctgcacat    5760
attattctgt acgggggaga cttttatttg caccctagct acctcggtat tcgcaggaaa    5820
cgtaaacgca tgcacaattt cttttcagat gtctatgtgg cggcctagtg actccaaggt    5880
ctacctacca cctgtcctgt gtctaaggtg gtcagcacgg atgaatatgt ctctcgcaca    5940
agcatatact atcacgctgg cagttccaga cttctggctg ttggacatcc ctactatgct    6000
gtaaagaagg gcaacaacaa agtgtcagtg cccaaggttt ctggtttaca ataccgagtg    6060
tttcgagtgc gtttgcctga ccccaataag tttggccttc cagatgctaa cttttatgac    6120
cctaacacac agcgccttgt gtgggcctgt ttaggcgtgg aggtggggcg tggacagcca    6180
ctgggagtgg gcaccagtgg tcatccactg ctgaacaaac tagatgacac ggaaaatggc    6240
cctaaagtgg ccgggggaca aggagcagat aacaggggaat gcgtgtcaat ggactacaag    6300
caaacacagc tgtgcatgct aggatgcaag cccctgtgg gtgagcattg gggaaaagga    6360
aatccttgca ccactggcgc tgcaggtgac tgccctgcac ttgagcttgt taactcagtt    6420
atacaggatg gggacatggt tgatacaggg tatggcgcta tggactttaa tgcactgcag    6480
gccaacaaat cagatgttcc tatagacata tgcactagcg tgtgcaaata ccctgactat    6540
ttaaaaatgg catcagatcc ctatggcgac agcttgtttt tttacctgcg aagggagcaa    6600
atgtttgtca gacacctgtt taacagagct ggcacaatgg gtgacagtgt ccctgatgac    6660
ttgtatatta aaggcagtgg aagcaatgtc aagcttgcca gccacgtgtt ttaccccaca    6720
cctagtggct caatggtgac atctgatgcc caattattta acaagccata ctggttacag    6780
aaagcccagg gccataacaa tggcatctgt tggggcaacc aagtgttcct tactgtagtt    6840
gacaccacta ggagcacaaa catgacactg tgtgcatcca ctgcctccac agttactaca    6900
ccatataata atgagagttt taaagagtac ctgcgacatg tggaggagtt tgatttgcaa    6960
tttatatttc agctgtgcaa ggtaacccctg aacactgaag taatggccta catacacagc    7020
atggatgcca gcatactgga ggactggaac tttggttttgc agcctcctcc gtctggctcc    7080
ttgcaggaca cctataggtt tgtgacgtct gccgccatca cctgtcaaaa acctgcaccc    7140
cccaaagaaa aggaagaccc gttggctaag tataccttt gggaggtgga tttaaaggaa    7200 aagtttctg cagatttaga ccaatttccc ttaggccgca aattttttgct gcaagctggc    7260 atgcgtgcac gccctaccct gcgcgccccc aaacgcacag cctcatctac ctcatcttcc    7320 agccccgca acgcaaacg caccaaacgc taacgttgct tatatttatg ttgttgtacc    7380
cagtgtgcat gatttatgta tgtgtgcatg ttgtacgtga ttttgtattt cctgtgttgt    7440
gcgtgtcact gttttgtgtt gttgcgtgag tgtgttgcac ttatgtgttt attaaagtat    7500
```

```
gcgtggtcgc acccgagtga gtaactgtgt gtgtccggcg tgtagtttct gtcacatgca    7560
tgcatgcaca cccaaacact gttgccactg cctttaacag cttgcctgct gcacttccat    7620
tttgaaccct tctccatttt ccctgcaaac cctccatttt atggtctcga ccggtttcgg    7680
tcgcgcttgg cacgcatttt gggcaaacaa aaccacaaca ctgctaatcc tctggcttcc    7740
tgcctctcct actgctgcat acctgtggtt gtgctttggc gctccctggt gactcactgt    7800
ctctgcaaac aaaaatttgc acacacactt aatccaaccc tctttgtaca aaatgctttt    7860
ggcagtacat ttctaagagt tactcatgct aattgcatag ttggccacaa tttcaggggtt   7920 ggattgccaa tactatgtcc ttttaaatgt gattaatttt caaaatgttc ttgcaggtgt    7980
gtgtgaccgg gatcggtcaa actttcacaa gcattttta tagtaa                    8026
```

RHPV AS A MODEL FOR HPV-INDUCED CANCERS

CROSS REFERENCE TO RELATED APPLICATIONS

This application claims benefit of U.S. Provisional Application 60/515,476, filed Oct. 29, 2003, which is incorporated by reference herein to the extent that there is no inconsistency with the present disclosure.

ACKNOWLEDGEMENT OF FEDERAL RESEARCH SUPPORT

The United States Government has a paid-up license in this invention and the right in limited circumstances to require the patent owner to license others on reasonable terms as provided for by the terms of Contract No. CA 85747 and No. R21-CA103645 awarded by the National Cancer Institute of the National Institutes of Health of the United States Department of Health and Human Services.

BACKGROUND OF THE INVENTION

The present invention relates to a non-human primate animal model infection system for the study of human papillomavirus (HPV) induced anongenital (including cervix, anus, penis), and potentially head-and-neck cancers, in particular the Rhesus papillomavirus (RhPV), cloned RhPV1 viral DNA and Rhesus cell culture models of infection.

Papillomaviruses (PVs) are a large family of nonenveloped, icosahedral DNA viruses with a particle diameter of 50-55 nm. PVs display remarkable species specificity and strong cellular tropism, and produce benign and malignant tumors in their natural hosts (8, 10, 14). Humans are the only known hosts for human papillomaviruses (HPVs); attempts to transfer HPVs to other species have failed (15). Complete genomes have been cloned for over 85 types of HPVs; 130 additional types have been partially characterized by PCR techniques (4). Only certain types of HPVs are associated with human cancers. For example, HPV1 and HPV2, types generally found in common and plantar warts, are not associated with carcinomas. HPV6 and HPV11, associated with laryngeal papillomatosis and anogenital lesions, rarely lead to carcinomas. The latter are known as low-risk viruses (2, 5). HPVs commonly associated with malignant conversion include those involved in epidermodysplasia verruciformis (e.g., HPV5 and HPV8) and a subset of the types that infect the anogenital region. Examples of the high-risk anogenital viruses include HPV types 16, 18, 31, 33 and 51 (1, 2, 5, 6). High-risk HPV infections are involved in greater than 99% of all anogenital malignancies (Walboomers, J. M. M., M. V. Jacobs, M. M. Manos, F. X. Bosch, J. A. Kummer, K. V. Shah, P. J. F. Snijders, J. Peto, C. J. L. M. Meijer, and N. Muñoz. (1999) Human papillomavirus is a necessary cause of invasive cervical cancer worldwide. J. Pathol. 189: 12-19), and cervical cancer is the second leading cause of cancer-related deaths in women worldwide (13). High-risk HPVs are also associated with head-and-neck cancers (Gillison, M. L., W. M. Koch, R. B. Capone, M. Spafford, W. H. Westra, L. Wu, M. L. Zahurak, R. W. Daniel, M. Viglione, D. E. Symer, K. V. Shah, and D. Sidransky. (2000) Evidence for a Causal Association Between Human Papillomavirus and a Subset of Head and Neck Cancers. JNCI Cancer Spectrum 92: 709-720) The capacity of HPVs to cause malignancies can be partially attributed to their ability to establish persistent infections (7). Thus, high risk HPVs pose a serious public health problem.

Viral particles from high-risk HPV types are produced only in small amounts in vivo (Pfister, H. (1984) Biology and biochemistry of papillomaviruses. Rev. Physiol. Biochem. Pharmacol. 99: 111-181) and the ability to obtain quantities of virions necessary for infectivity studies has been severely limited for high-risk HPVs, inhibiting many studies of HPV biology. There have been no reports of viral particle isolation from the typically small anogenital lesions that can progress to malignancies. This has inhibited many studies of PV biology. The organotypic (raft) tissue culture system is the only in vitro system proven to consistently mimic epithelial differentiation to the extent that infectious high-risk PVs can be purified.

There is currently no animal model system to study genital PV infections in vivo. However, a PV genome was recently recovered from a rhesus monkey with a metastatic tumor arising from a penile carcinoma (12). This virus, named RhPV1 for rhesus PV type 1, was found to be sexually transmitted among rhesus monkeys (12). Only four papers have been published on this RhPV1 genome. The first paper describes the discovery and initial cloning of the genome from a male with a lymph node metastasis of a squamous cell carcinoma of the penis (9). In the second paper, the authors determine the biological significance of the genome by showing RhPV1 infections occurred in a population of female monkeys who were sexually active with the index male (12). The third paper describes the characterization of the genome and its integration locus in the host DNA (11). The fourth paper looks at the evolutionary conservation of this viral genome and determines that RhPV1 is closely related to HPV types 16, 31, and 33, causes of human anogenital and head-and-neck cancers (3).

There is a longfelt need in the art for an animal model, especially a non-human primate animal model, infection system, in which to study of PV infection and PV-induced (i.e. all) anogenital cancers. Such a system would permit the study of the natural history of PV infection, including transmission, immunology, acute and chronic pathology (neoplasia), and progression to malignancy of PV infections, as well as testing of potential prophylactic and therapeutic agents. This model will also likely have great impact on our understanding of the role of HPVs in head-and-neck cancers. The present invention using RhPV fulfills this need.

SUMMARY OF THE INVENTION

The present invention provides an animal (Rhesus macaque, *Maccaca mulatta*) model system for the study of PV-induced cervical lesions. One aspect of the invention is the production of infectious Rhesus papillomavirus virions in raft cultures as follows. While the present disclosure specifically exemplifies RhPV1, other RhPVs which are high risk for causing cancers can be substituted for the RhPV1 in the present methods for virion production, screening for inhibitors of PV infection and replication, PV physiology and animal infections. Cloned RhPV1 viral DNA is released from the plasmid vector and transfected into permissive cells. Four types of cells may be used: human immortalized HaCaT cells that can support the HPV life cycle; human foreskin keratinocytes which can support the HPV life cycle; Rhesus cervical cells; or rhesus foreskin keratinocytes. Pooled or clonal cell lines that contain replicating RhPV1 viral DNA are established as long-term or stable cultures. When grown in the organotypic (raft) tissue culture system, these cells differentiate and will produce infectious RhPV1 virions that can be purified and used for experimental infections, both in vitro and in vivo. Advantageously, the cultures producing the virions are heat-shocked at 43° C. for 90 m on day 6, 8, and 10 following lifting of the raft tissues to the air-liquid interface. Temperatures from 41 to 43° C. and times from 90 to 120 minutes can be used, or other conditions known to art which induce the expression of Hsp40 and Hsp70 can be used to increase PV virion expression. The tissue are harvested at 10-12 days post lifting and Virions are collected as previously described The heat shock step improves virion yield from at least 10 to as much as 100 fold. This heat shock treatment is applicable to the improved production of infectious virions in other papillomavirus cultures as well, including but not limited to human, other primates, bovine, and cottontail rabbits.

It is a further aspect of the invention to provide an animal model system and an animal model culture system (as specifically exemplified, raft cultures of Rhesus cervical or foreskin keratinocytes) to provide RhPV1-infected cell cultures in which to test potential therapeutic compounds which inhibit virus production and/or viral infection. Raft cultures are incubated in the presence and absence of a potential inhibitor. A compound is identified as inhibiting virus infection and/or production when the infected cells or virus yield is lower in the raft cultures than in the untreated control culture.

A major aspect of the invention is to provide the animal system for examining experimental infections in vivo, specific aspects that cannot technically or ethically be studied in human infections. These include the types of sexual or nonsexual behaviors that promote transmission, the time course of infection from incident to detection of viral effects (viral genomes, viral transcripts), the initial immune response to incident infection, the variability of infection due to host genetics, the time course to potential infection clearance or progression to neoplasia, the time of progression to malignancy, and testing of potential prophylactic and therapeutic agents.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are for the purpose of illustrating one or more embodiments of the invention and are not to be construed as limiting the invention.

FIG. 2A illustrates epithelial cells are seeded onto submerged type I collagen matrices containing fibroblasts, typically in 6-well plates. In FIG. 2B, when the epithelial cells reach confluence, the growth medium is removed, and the collagen matrices are lifted onto stainless steel support grids in 100-mm dishes. FIG. 2C illustrates the collagen matrix on the support grid suspends the epithelial cells as a "raft" at the air-liquid interface promoting differentiation. The epithelial cells are fed by diffusion from below the air-liquid interface; the collagen-fibroblast matrix acts as the dermal equivalent. FIG. 2D shows that epithelial tissues are allowed to stratify and differentiate over a 2-week period. The raft system is the only in vitro system proven to consistently mimic epithelial differentiation to the extent that infectious papillomaviruses can be purified.

FIG. 5A: levels of Hsps in 9E raft tissues following no heat shock; heat shock (43° C., 90 minutes) on day 6; days 6,8; or days 6,8,10 (as indicated at top) after lifting to the air-liquid interface. Raft tissues were harvested for total proteins on days 6, 10, and 14 after lifting. Hsp levels were analyzed by immunoblot using commercially available antibodies (Stressgen Biotechnologies Corporation, Victoria, BC, CA). FIG. 5B: HPV31b virion production in 9E raft tissues following heat shock; rafts were harvested for virion production on day 14 after lifting. Heat shock (HS) treatments were as indicated. Virion quantification (numbers are shown below each bar) was determined by dot blot hybridization reflecting the number of viral genome equivalents (VGE) per raft. FIG. 5C: Infection correlates with VGE quantities in HPV31b virion preps obtained following 9E raft growth in the absence or presence of heat shock on various days. HPV31 b stocks were derived from rafts as indicated in Table 1 and FIGS. 5A-5B above, and used to infect HaCaT cells. Total RNAs (3 μg) were subjected to RT. RNAs were analyzed from 9E monolayers (9E), mock-infected HaCaT cells (Mock), HaCaT cells infected with viral doses (MOI) corresponding to 0.01, 0.1 1.0, and 10 VGE per cell. No RNA input (Ø) was a negative amplification control. RT reactions were divided into PCR amplifications. (Top) Primers target a 502-bp amplimer resulting from spliced Hpv31b E1*I,E2 RNA; (bottom) Primers detect a 641-bp amplimer derived from spliced β-actin RNA as an RT control (see Ozbun, M. A. (2002) J. gen. Virol. 83: 2753-2763 for detail on infections and assays).

DETAILED DESCRIPTION OF THE INVENTION

Figure 1:
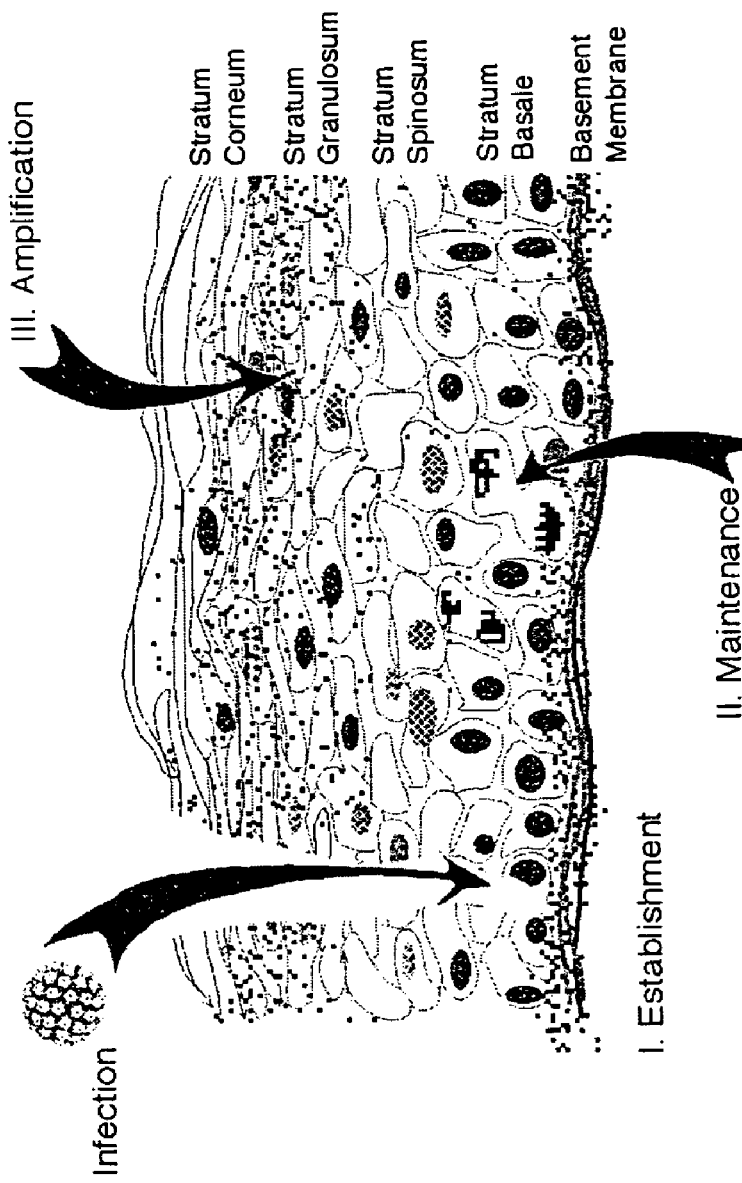
FIG. 1 depicts a model for PV infection in a stratified epithelium. The three stages of viral genome replication are indicated; major viral functions are noted at the right side. Infection of the mitotically active basal cell layer is believed to be necessary for the establishment of viral persistence in these stem cells. Stages I and II occur in the lower, undifferentiated cells. As cells migrate up through the epithelium, they undergo a complex program of differentiation. Stage III occurs predominantly in suprabasal cells and is the vegetative DNA replication (amplification) phase. Late gene expression is restricted to the upper, differentiated layers of the epithelium; concurrent vDNA amplification and late gene expression lead to vDNA packaging and virion morphogenesis.
Figure 2A:
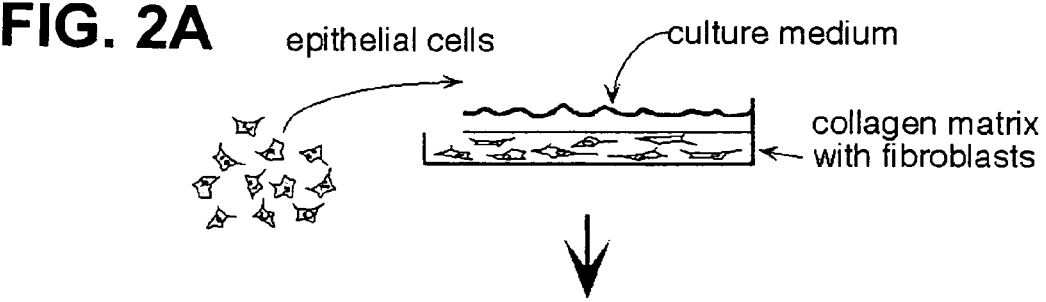
FIG. 2A-2D provide an illustration of the organotypic (raft) culture system.
Figure 2B:
Figure 2C:
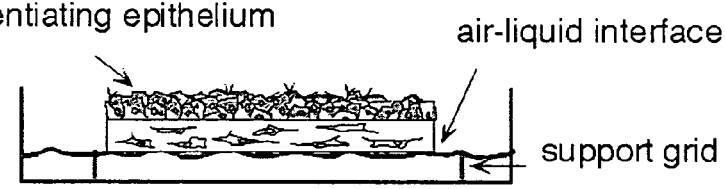
Figure 2D:
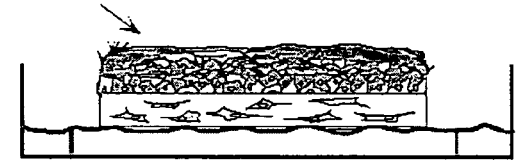
Figure 3:
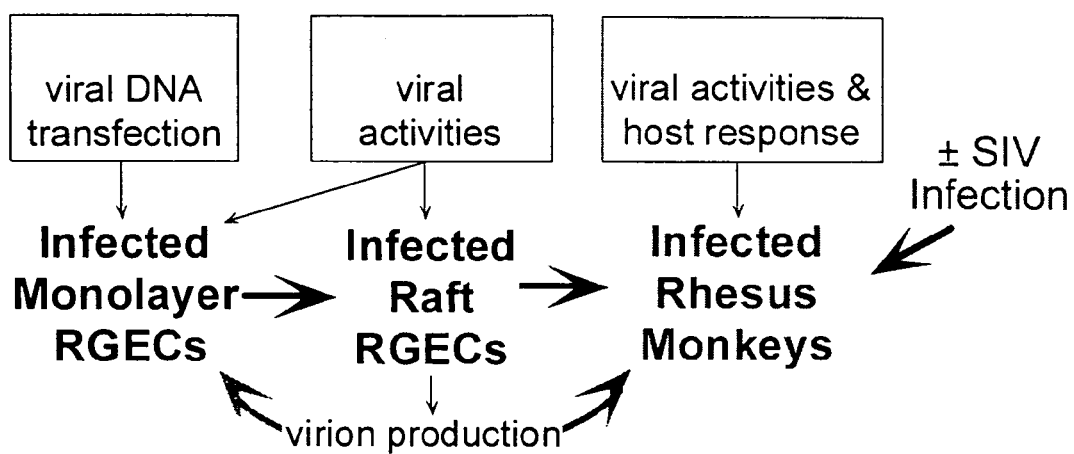
FIG. 3 illustrates model systems for anogenital PV infections. Transfected Rhesus genital epithelial cells (RGECs) permit the complete RhPV1 life cycle in undifferentiated monolayer cells and in differentiated raft tissues to be studied. RhPV1 virions can be produced in the raft system and can be used to infect low passage RGECs and the genital tracts of live Rhesus macaques for the characterization of viral and cellular activities. The characterization of viral activities in this system will reveal viral activities to target for in vivo work. Thus in this model system the entire PV life cycle can be studied, from virion production in vitro, to infection of live Rhesus macaques in vivo and assessment of host and viral responses, followed by virion production in vivo.

As noted herein, the use of RhPV1 is described, but other RhPVs with a significant risk for anogenital cancers and/or head and neck and respiratory cancers, can be used in the methods of the present invention. The RhPV1 genome is introduced by transfection into cell lines from human or Rhesus monkey origin. The viral genome replicates as an episomal (extra-chromosomal) DNA and expresses viral gene products. The cells containing replicating viral DNA are grown in the organotypic (raft) tissue culture system and the cellular differentiation promoted in the raft system supports the complete viral life cycle and allows infectious virions to be biosynthesized. Infectious virions are used to infect human or rhesus monkey cells in culture and to infect the anogenital tracts or airway epithelial tissue of live rhesus monkeys (male and female). This results in an animal model system for the study of the natural history of PV infection, including transmission, immunology, acute and chronic pathology (neoplasia), and progression to malignancy of PV infections. This model can be used to test prophylactic and therapeutic agents.

Prior to this invention it is believed that it was not possible to characterize the RhPV1 life cycle (RNAs, viral DNA replication, production of infectious virions, experimental infection either in vitro or in vivo). Similarly, no one had been successful in replicating a non-human PV in human cells or a human PV in non-human cells. Similarly, it is believed that in the past no one had isolated infectious RhPV1 virions either from animals or from cells grown in culture and no one had established a non-human primate model for HPV-induced anogenital or head-and-neck malignancies. The present invention provides an animal model system for the study of PV-induced cervical lesions. The practice of the invention is as follows. Cloned RhPV1 viral DNA is released from the plasmid vector and transfected into cells. Four types of cells may be used: human immortalized HaCaT cells that can support the HPV life cycle; human foreskin keratinocytes which can support the HPV life cycle; Rhesus cervical cells; or rhesus foreskin keratinocytes. Pooled or clonal cell lines that contain replicating RhPV1 viral DNA are established as long-term or stable cultures. The stable cell lines are tested for viral replication by a number of means: RT-PCR for spliced viral transcripts, Real-time PCR or Southern blot hybridization to determine the episomality and copy number of the viral genomes; growth in the organotypic (raft) tissue culture system for the production, purification, and characterization of virus particles; characterization of infectivity: infection of the cell lines as described above and assay for spliced viral transcripts by RT-PCR; infection of live rhesus monkeys and follow-up analysis for viral DNA, viral transcripts, pathology by PAP smear, for example.

A non-human primate animal model infection system for the study of HPV-induced anogenital or head-and-neck cancers can be employed in a variety of clinical research settings. The animal infection model system of the invention permits the study of the natural history of PV infection, including transmission, immunology, acute and chronic pathology (neoplasia), and progression to malignancy; assessment of prophylactic agents for skin diseases and cancer, especially cervical cancer; evaluation of therapeutic agents for skin diseases and cancer, especially cervical cancer; characterization of host immunological responses to potential prophylactic or therapeutic agents; and elucidation of the molecular bases for the effectiveness of potential prophylactic or therapeutic agents.

In a preferred embodiment, the invention employs the Rhesus PV type 1 (RhPV1), a PV causing sexually transmitted anogenital cancers in Rhesus monkeys. The RhPV1 virus sequence analysis revealed this genome to be genetically very similar to HPV16 and HPV31, which are the HPV types that cause the majority of anogenital cancers in humans. The RhPV1 model can thus be employed to elucidate the molecular mechanisms used by PV to establish genital infections with a high risk of progressing to malignancy. The present invention provides a novel Rhesus macaque model in which to study anogenital PV infections and the pathogenesis of anogenital cancers. As anogenital cancers are particularly common among patients with human immunodeficiency virus (HIV) infection and the acquired immunodeficiency syndrome (AIDS), the model may be employed alone or in the context of AIDS induced by simian immunodeficiency virus (SIV) infections.

In another embodiment, the invention provides for efficient virion production from raft tissues or in vivo tissues, including use of a biologically contained Teflon homogenization device to grind tissues and release virions (rather than grinding in sand). As HPVs are human oncogenic viruses and are associated with head-and-neck cancers, it is of utmost importance to increase biological containment with reduced aerosolization for the purification of concentrated PV stocks that could potentially infect humans. The invention further provides a simplified virus purification method which omits CsCl density gradient centrifugation as a purification step. The invention further provides for directly analyzing the virions for DNA by treating with NaOH, rather than by performing an enzymatic digestion of purified DNA. The invention further provides for quantifying viral DNA in virus preparations using a simple dot blot procedure rather than a more lengthy agarose gel electrophoresis followed by Southern blot and hybridization. Radioactive or non-radioactive methods to detect viral DNA can be employed. In yet another embodiment, the invention provides a streamlined and more specific infectivity assay based upon using nested-PCR rather than PCR with Southern blot.

The use of the animal model system of the invention provides benefits including the ability to define molecular viral and cellular mechanisms that control the establishment of genital PV infections with a potential for malignant progression; assessment of potential prophylactic and therapeutic agents for PV-related diseases, especially anogenital cancers; characterization of host immunological responses to viral infection and potential prophylactic or therapeutic agents; elucidation of the molecular bases for the effectiveness of potential prophylactic or therapeutic agents; studies of the pathogenesis of mutant RhPV1 viruses in vivo created by reverse genetics; studies of anogenital PV infections in the context of AIDS induced by simian immunodeficiency virus (SIV) as a model for PV-induced cancer in AIDS patients.

The present animal model system provides for examining experimental infections in vivo, specific aspects that cannot technically or ethically be studied in human infections. These include the types of sexual or nonsexual behaviors that promote transmission, the time course of infection from incident to detection of viral effects (viral genomes, viral transcripts), the initial immune response to incident infection, the variability of infection due to host genetics, the time course to potential infection clearance or progression to neoplasia, the time of progression to malignancy, and testing of potential prophylactic and therapeutic agents.

According to current models, PVs infect the mitotically active basal epithelial cell layer in vivo through a microabrasion or wound in the epithelium. The complete viral replication cycle results in the production of virions (i.e., infectious progeny) and is tightly linked to the differentiation state of the infected cells. Epidermal cells are not fully permissive for PV replication at the onset of their cellular differentiation process, but become permissive with increasing differentiation. Viral genomes are replicated in three stages. In stage I the autonomously replicating episomal viral DNA (vDNA) is established at low (10-200) copy number per cell in the basal stem cells. This event is necessary for establishing viral persistence. Stage II occurs randomly during the cell cycle and provides daughter cells with an approximately equal copy number of the viral genome. Stage III yields amplified copies of vDNA in differentiating cells. Epithelial differentiation also results in the induction of late gene synthesis, leading to genome packaging and virion morphogenesis in the upper layers of the epithelium. Virions are shed with the desquamating epithelium to begin a new round of infection.

In anogenital epithelium in vivo, productive HPV infection is thought to occur only in benign or lower grade lesions referred to as condylomata acuminata, cervical intraepithelial neoplasia grade 1 (CIN-1), or anal intraepithelial neoplasia grade 1 (AIN-1). Very little is known about HPV activities in anal tissues compared to lesions in the female genital tract. Low-grade cervical lesions are slightly altered in their differentiation scheme compared with normal epithelium. In higher grade cervical lesions (e.g., CIN-3, carcinoma in situ, or invasive carcinoma) the cells remain undifferentiated, the HPV DNA may be at high levels and/or may be integrated into the host genome, and virion production is not observed. The integration of vDNA typically disrupts the E1/E2 ORFs presumably resulting in the deregulated expression of the E6 and E7 oncoproteins. This is believed to be an important event in the progression to malignancy.

Viral stocks can be readily purified from cutaneous skin lesions caused by the bovine PVs (BPVs) and cottontail rabbit PV (CRPV); but the ability to obtain quantities of HPV virions necessary for infectivity studies has been severely limited. Viral particles from most HPV types are produced only in small amounts in vivo. The number of virus particles in various human warts differs considerably, ranging from fewer than $10^3$ particles per mg of laryngeal papillomas (likely HPV6 or 11) to $7 \times 10^9$ particles per mg of some plantar and common warts (likely HPV1 or 2). The purification of virus particles from the typically much smaller anogenital lesions has not been reported. This has inhibited many studies of HPV biology. Purification or production of RhPV virions has not been reported.

Because the viral life cycles are dependent upon cellular differentiation, it has been challenging to cultivate and analyze various types of PVs in the laboratory. There are in vivo systems using athymic mice for study of the PV life cycle. Kreider et al. purified infectious HPV11 using the xenograft system whereby virus is inoculated into susceptible human epithelial tissue chips (usually foreskin tissue) and grafted under the renal capsule of an athymic mouse. HPV1, HPV16, HPV40, and CRPV also can be produced in the xenograft system. In one report, HPV16 particles were observed following the grafting of CIN-1 biopsy-derived W12 cells onto the granuloma beds in the flanks of nude mice, but viral particles were never purified. In a second report, infectious HPV16 virions were produced from CIN tissue in xenografted SCID mice. The use of immune-compromised animals for these studies prevents systematic analyses of PV infections and biology in the context of an intact, normal animal. Furthermore, it has not been technically possible to analyze xenograft tissues at the initial stages of infection.

Some aspects of keratinocyte differentiation and differentiation-dependent HPV replication can be achieved by suspension of HPV-infected keratinocytes in a semisolid methylcellulose-containing medium. For example, vegetative (stage III) vDNA replication has been studied. However, the suspension cultures fail to express keratin 10 (K10) and filaggrin, important markers of differentiation, and the synthesis of the viral major capsid protein L1 has not been reported in those cultures.

Organotypic (raft) culture techniques have greatly benefited PV research (FIG. 2). The differentiation achieved in raft cultures gives rise to an environment which is permissive for the complete viral life cycle. The raft system is the only in vitro system proven to consistently mimic epithelial differentiation to the extent that infectious PVs can be purified. Growth of CIN-612 9E raft tissues results in the reproducible production of HPV31 (HPV31a and HPV31b subtypes) virions that can be purified. The majority of information on high-risk HPV life cycles has come from analyses of HPV31 in raft tissues. Hummel et al. reported polycistronic early and late gene transcripts of HPV31 and described a major early promoter ($P_{97}/P_{99}$) and a differentiation-dependent promoter, $P_{742}$. These studies have been extended with temporally analyzing the expression of the early and late gene transcripts during the latter stages of the HPV31 life cycle in raft tissues. Infection of human epithelial cell (HEC) lines by HPV31 with early viral RNAs detected as early as 4 h post infection (p.i.) have been reported by the present inventor. Seven novel viral RNAs were detected in these studies. The structures and temporal expression patterns of 22 differentially spliced early transcripts and 19 late gene transcripts for HPV31 have been characterized as well as the temporal expression from 8 HPV31 promoters.

Little is known about the early stages of the genital PV infections either in vitro or in vivo, and little is known about effective treating or preventing papillomatosis. The study of the basic biology of PVs has been severely limited, especially assessment of the early phases of infection and investigations of the mechanisms by which PVs establish persistent infections with a high risk of malignant progression. The methods of the invention provides for study of RhPV1 viral activities following experimental infections in vitro. There is currently no technically feasible or ethical way to monitor the initiation of HPV infection and the cellular and systemic responses to such infections in vivo. The invention thus provides a renewable source of infectious RhPV1 virions and the knowledge of viral activities in vitro. These are important tools that may be employed to study the natural history of PV-induced anogenital malignancies in vivo. This invention thus provides a novel non-human primate animal model with which to study both viral and host activities involved in persistent PV-induced anogenital infections.

The invention accordingly provides methods and an animal model system in which to elucidate the molecular mechanisms by which PV establishes anogenital infections with a high risk of progressing to malignancy. The Rhesus monkey model permits the study of anogenital PV infections and the pathogenesis of anogenital cancers in the context of an intact animal. The model may also be used in the context of simian AIDS induced by SIV infections. Using the methods of the present invention, persistently PV-infected cell lines are created by transfection of cloned PV genomes. The complete life cycles of PVs in infected epithelial tissues grown in the organotypic (raft) tissue culture system are studied. It is further possible to purify infectious viral stocks of high-risk PV types from the raft system and demonstrate experimental infections in cultured epithelial cells and in Rhesus macaques. The Rhesus cell culture and animal model system allows the testing of therapeutic and/or prophylactic regimens.

Heat shock proteins (Hsps, also known as "cellular stress proteins" and "molecular chaperones") are a family of proteins classified into six major families according to their molecular size: Hsp100, Hsp90, Hsp70, Hsp60, Hsp40, and small Hsps like Hsp27 (Jolly, C. and R. I. Morimoto. (2000) J Natl Cancer Inst, 92: 1564-1572). Hsps are expressed in response to heat stress, oxidative stress, bacterial and viral infections, inflammation, toxic chemicals, and other cellular stresses including cancer (reviewed in Jolly and Morimoto (2000) supra). Specifically, the chronic infection by and inflammatory damage caused from Chlamydia infection induces Hsp expression (Debattista et al. (2003) Fertility and Sterility 79: 1273-1287). Furthermore, NO exposure induces the expression of several Hsps, including Hsp32, Hsp70, and Hsc70, the constitutive Hsp (reviewed in Chung, H.-T (2001) Biochem. Biophys. Res. Commun. 282: 1075-1079).

Hsps interact with diverse proteins substrates to assist in their folding especially during cell stress to prevent misfolded or otherwise damaged molecules. Consequently, these proteins assist in recovery from stress by either repairing damaged proteins (refolding) or by promoting their degradation, thereby supporting cell survival. The events of cell stress and cell death are linked, such that molecular chaperones induced in response to stress appear to function at key regulatory points in the control of apoptosis. Hsp70 appears to have multiple roles in protection of cells from apoptosis (Jolly, C. and R. I. Morimoto. (2000) J Natl Cancer Inst. 92: 1564-1572; Xanthoudakis, S. and D. W. Nicholson. (2000) Nat Cell Biol, 2:E163-E1655), and can render cells resistant to NO-mediated apoptosis (Jadeski, L. C et al. (2002) Can. J. Physiol. Pharmacol./Rev. Can. Physiol. Pharmacol. 80: 125-1353). Exposure of hepatocytes to SNAP induces Hsp70 expression, which protects the cells from apoptosis (Kim, Y.-M et al. (1997) J. Biol. Chem. 272: 1402-1411). Hsp27 can also prevent apoptosis, whereas Hsp10, Hsp60, and Hsp90 have pro-apoptotic activities (Xanthoudakis, S. and D. W. Nicholson. (2000) Nat Cell Biol. 2:E163-E1655). Although altered Hsp expression is found in nearly every tumor type, it is not clear whether the association is causal or correlative. Little is known about how Hsps protect cells from apoptosis, and their ability to do so, especially in the context of malignant progression, requires additional studies.

Hsp are involved in many steps in the life cycles of various viruses, particularly those that abrogate apoptosis. Cellular or virally-encoded stress proteins cause altered transcription, cellular transformation, viral genome replication, and increased virion assembly (reviewed in Sullivan, C. S. and J. M. Pipas. (2001) The virus-chaperone connection. Virology 287: 1-8). The connection between HPV replication and stress proteins is poorly understood. The HPV E7 oncoprotein interacts with host cell stress proteins hTid-1 and Hsp-E71; these interactions appear to dissociate the pRb-E2F complex to induce proliferation and cellular transformation (Morozov, A. J. et al. (1995) FEBS Letters 371: 214; Schilling, B. et al. (1998) Virology 247: 74-8511). Increased expression of stress proteins Hsp40 and Hsp70 enhance the binding of the HPV E1 replication factor to the viral origin of replication, abrogate E2 inhibition of E1, and promote a subsequent increase in viral DNA replication (Lini, B. Y. et al. (2002) Mol Cell Biol. 22: 6592-6604; Liu, J. S. et al. (1998) J. Biol. Chem. 273: 30704-307126). Evidence from closely related polyoma and SV40 viruses suggests that stress proteins are involved in virion assembly (Sullivan, C. S. and J. M. Pipas. (2001) Virology 287: 1-812).

Figure 5A:
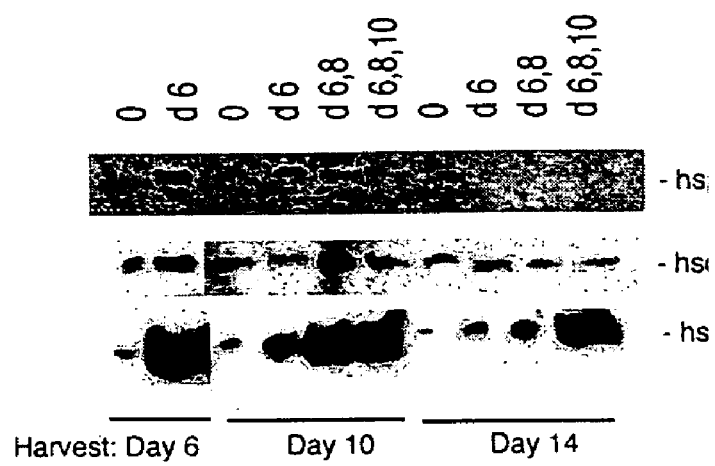
FIGS. 5A-5C show that heat shock induces Hsps and correlates with increased virion production in 9E raft tissues.
Figure 5B:
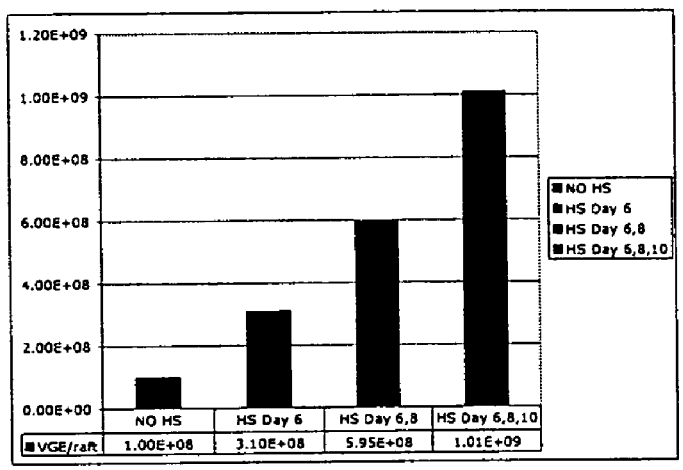
Figure 5C:
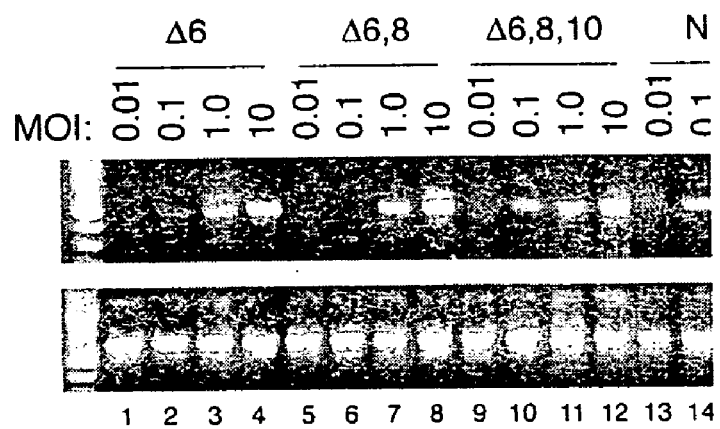

These data prompted us to test our hypothesis that an increase in stress protein levels in differentiating epithelial cells infected with HPV would result in an increase in viral DNA replication and virion production. Experiments using 9E raft tissues corroborated this hypothesis. Differentiating epithelial tissues were exposed to heat shocks on various days and numbers of days as the HPV-infected cells were allowed to differentiate at the air-liquid interface in the raft system. Tissues were harvested for total DNA, for total protein, and for virions. Immunoblot analyses demonstrated that Hsp70 was highly up regulated in response to heat shock. Expression of Hsp40 was up regulated slightly by heat shock (harvest at days 6 and 10), but was down regulated upon epithelial differentiation (harvest on day 14). Although the levels of Hsp70 and Hsp110 were not detectably altered, a cursory analysis of cytoplasmic versus nuclear protein fractions by immunoblot indicated that Hsc70 moved from the cytoplasm into the nucleus upon heat shock. The increases in Hsp70 and Hsp40 levels were coincident with increased viral genome replication in raft tissues measured by Southern and dot blot hybridization and increased virion production (FIGS. 5B, 5C). Heat shocked raft tissues were harvested at 14 days after lifting for virion production, which is measured by quantification of vDNA in purified viral particles (viral genome equivalents, VGE) and verified by infectivity assay as we have reported (Ozbun, M. A. (2002) J. Virol. 76: 11291-11300; Ozbun, M. A. (2002) J. gen. Virol. 83: 2753-2763) (FIG. 5C). Most striking was an approximately 10-fold increase in virion production concurrent with increased stress protein levels and increased viral genome replication. HPV31 b-infected tissues heat shocked on days 6, 8, and 10 yielded $1.0 \times 10^9$ VGE per raft tissue, whereas no heat shock yielded $1.1 \times 10^8$ VGE (FIG. 5B). These data indicate that an increase in Hsps, especially Hsp70 and Hsp40, has a dramatic positive effect on HPV replication and virion production in differentiating epithelium.

Monoclonal or polyclonal antibodies, preferably monoclonal, specifically reacting with a protein of interest may be made by methods known in the art. See, e.g., Harlow and Lane (1988) Antibodies: A Laboratory Manual, Cold Spring Harbor Laboratories; Goding (1986) Monoclonal Antibodies: Principles and Practice, 2d ed., Academic Press, NY.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; and Setlow and Hollaender (1979) Genetic Engineering: Principles and Methods, Vols. 1-4, Plenum Press, New York. Abbreviations and nomenclature, where employed, are deemed standard in the field and commonly used in professional journals such as those cited herein.

All references cited in the present application are incorporated by reference herein to the extent that they are not inconsistent with the present disclosure.

The following examples are provided for illustrative purposes, and are not intended to limit the scope of the invention as claimed herein. Any variations in the exemplified articles which occur to the skilled artisan are intended to fall within the scope of the present invention.

Patents and publications mentioned in the specification are indicative of the levels of skill of those skilled in the art to which the invention pertains.

One skilled in the art would readily appreciate that the present invention is well adapted to carry out the objects and obtain the ends and advantages mentioned, as well as those inherent therein. The compounds and methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

All references cited herein are hereby incorporated by reference to the extent that there is no inconsistency with the present specification.

The invention is further illustrated by the following non-limiting examples.

EXAMPLE 1

HPV18 Transfection Into Low Passage Normal HECs

The biosynthesis of infectious HPV18 was performed by allowing low passage HECs transfected with cloned HPV18 DNA to differentiate in the raft system. Both foreskin and ectocervical cells were tested with similar results. We selected a clonal outgrowth of the transfected HECs, HCK18:1Bj, that contains ≈50 episomal copies of HPV18 per cell. The clonal HCK18:1 Bj cells were grown as raft tissues and viral particles were purified by a series of low and high speed centrifugation steps. Southern blot analysis of HPV18 virus particle preparations indicated the purification of ≈$10^8$ HPV18 particles per raft tissue (a total of 1.5 ml at $1.5 \times 10^9$ particles per ml). The infecting dose for PVs is based on the number of vDNA-containing particles. Hereafter, the term "virion" is employed to refer to vDNA-containing PV particles. The HPV18 virus particles were shown to be infectious by incubating subconfluent HEC monolayers with a dose of ≈340 particles per cell; spliced HPV18 transcripts were detected by RT-PCR analyses.

EXAMPLE 2

HPV31 Transfection Into Low Passage Normal and Immortalized HECs

HPV31 DNA transfection into low passage HECs (stable cell line HK31a) or the immortalized HEC lines SCC-13 and HaCaT resulted in the production of viral particles. Transfection of high-risk HPV genomes into low passage (mortal) foreskin or cervical HECs results in immortalization of these cells in the presence of stable, episomally replicating viral genomes. The theory is that the HPV genomes express early gene products (probably E6 and E7) that give the cells a growth advantage and extend the life span of the cells. However, co-transfection of a selectable marker (e.g., the hygromycin resistance gene) is necessary to select for stable HPV transfectants when immortalized HEC lines like SCC-13 and HaCaT are used. The HPV-negative SCC-13 cell line is an immortalized line derived from a squamous cell carcinoma of the facial epithelium. Patches of intranuclear HPV31 virus particles were observed by electron microscopy in the suprabasal layers of the transfected SCC-13 raft tissues. Treatment of SCC-13 raft tissues with protein kinase C inducersi or with transforming growth factor β1 results in increased morphological and biochemical differentiation as measured by immunohistochemical staining for differentiation markers such as K10 and filaggrin. These treatments also increase PV late gene expression and virion production. HaCaT cells (a gift of N. Fusenig, DKFZ) are an immortalized HEC line derived from normal adult skin that display nearly normal differentiation as raft tissues. When HPV31-transfected HaCaT cells were grown as raft tissue and treated with protein kinase C inducers, we were able to purify virions and demonstrate them to be infectious. These data indicate that normal low passage HECs and immortalized HEC lines can be induced to differentiate and produce HPV virions in the raft tissue culture system.

EXAMPLE 3

RhPV1 Transfection into Low Passage Normal and Immortalized Hecs

In a preliminary study, the RhPV1 genome was transfected into low passage foreskin HECs and into HaCaT cells; stable selections were not performed. Viral transcription and replication were detected in these cells as assayed by detection of spliced viral transcripts corresponding to both E1*I,E2 and E1^E4 (FIG. 5) and an increased life span of the mortal foreskin HECs. Sequence analyses of RhPV1 cDNAs derived from RT-PCR amplimers revealed spliced E1*I,E2 and E1^E4 transcripts similar to those expressed by high-risk HPV types (e.g., 16 and 31;). These RhPV1 transcript data are the first collected from a non-human primate PV. Furthermore, these results indicate that the cloned RhPV1 genome is competent for replication in HECs and further suggest that RhPV1 will behave in a biologically similar fashion to its related high risk HPV types 16 and 31. Primary Rhesus genital epithelial cells (RGEC) have been obtained, and can used to stable RGEC and HEC lines that maintain episomally replicating RhPV1 genomes. These stable, persistently infected cell lines can be grown in the raft tissue culture system to induce epithelial differentiation and the production of infectious RhPV1 virions.

EXAMPLE 4

HPV31 Life Cycle in Undifferentiated Monolayer Cells and in Differentiated Raft Tissues HPV31 replication in CIN-612 9E monolayers and raft tissues has been the most thoroughly characterized of any HPV type. The expression of early and late gene transcripts during the latter stages (stages II-III) of the HPV31 life cycle in raft tissues and in monolayer cells was determined. The structures and temporal expression patterns of fifteen differentially spliced early transcripts and nineteen late gene transcripts for HPV31 b were characterized. The levels of most viral RNAs peak coincident with the first appearance of viral particles in the nuclei of suprabasal cells. Further, the ratio of E1 to E2 transcripts is greatest when vegetative vDNA amplification peaks in the raft tissues. The temporal expression from eight HPV31 promoters was also evaluated. The HPV31b early promoter to nt 99 ($P_{99}$) was precised mapped, and shown to be the major early promoter, expressed at relatively high and constant levels throughout the viral life cycle. Four novel promoters were characterized, $P_{-7375}$, $P_{49}$, $P_{77}$ and $P_{3320}$, also expressed constitutively, but at lower levels, throughout the viral life cycle. Furthermore, it was shown that two novel promoters, $P_{7783}$ and $P_{7850}$, were negatively regulated by differentiation, suggesting that they may be important immediately following infection. Late gene RNAs initiated in the region of $P_{77}/P_{99}$ and at $P_{3320}$. However, it was found that late gene transcription initiating at $P_{742}$ was responsible for the significant increase in late gene RNAs detected in differentiated raft tissues compared to undifferentiated tissue and cells. Studies of RhPV1 in stably transfected (persistently infected) RGEC and HEC can be modeled after these studies of HPV31 in CIN-612 9E monolayer cells and raft tissues.

EXAMPLE 5

Biological Containment During Virion Purification

A biologically contained homogenization system for efficient virion extraction from raft epithelial tissues was developed. Therefore, an efficient approach for extracting RhPV (or HPV) virions that was more biologically contained and that reduced aerosolization of this human pathogen was developed. The procedure relies on the use of the Bead-Beater™ device in which glass beads are enclosed in the mechanical Teflon® homogenization apparatus.

Purified HPV31 virions were used to infect low passage HECs and a variety of established HEC lines. As there is currently no way to quantitatively titer HPVs based upon infectivity, the dose of viral infection was defined based upon the number of vDNA-containing particles. Newly synthesized, spliced viral RNAs were detected as a qualitative indication of infection. Previous work showed detection of spliced viral RNAs to be a better indication of bona fide infection than detection of vDNA. This is because vDNA could be present in virions that were simply attached to cells, or the vDNA could reflect virions present in the cytoplasm of the cells. As PV virions do not contain spliced RNAs, the detection of spliced viral RNA requires de novo transcription of infecting vDNA in the nucleus. Newly synthesized, spliced HPV31 transcripts were detected by RT-PCR following HPV31 infection. It was found HPV31 infection to be most efficient and reproducible in HaCaT cells; infection could be detected at a dose as low as 1.0 vDNA-containing particle per cell in HaCaT cells and in low passage foreskin HECs. Based upon previous work characterizing HPV31 transcripts from persistently infected CIN-612 9E cells and raft tissues, the spectrum of transcripts and their onset following HaCaT cell infection was analyzed. Using RT-PCR techniques, spliced E1*I,E2 and E8^E2C RNAs were present as early as 4 h p.i., whereas other major early viral transcripts like E6*I and E1^E4 were detected by 8-10 h p.i. These experiments resulted in the characterization of seven novel spliced early transcripts expressed following infection. The ORFs created by these newly identified splicing patterns have the ability to yield viral peptides as small as 2.9 kDa. Larger ORFs created by splicing are predicted to be 9.9 kDa, 13.5 kDa, and 28.4 kDa. Small viral regulatory proteins are well known for other viruses; examples include the HIV Vpr and Nef proteins, the human polyomavirus agno proteins, and the hepatitis B virus X protein. HPV31 infected HaCaT cells were allowed to differentiate in the raft system and we detected late gene expression in these tissues. Similarly, infection of low passage HECs resulted in the production of intranuclear virus particles in suprabasal raft epithelial cells.

There currently is no quantitative assay for HPV infection; therefore, it is impossible to assess the number of infectious viral particles in our stocks or the number or percentage of cells infected by our PV stocks. However, rough estimations can be made based upon the infection parameters and experimental data. In further studies, we infected $3.5 \times 10^6$ cells with a dose of 20 particles per cell ($7 \times 10^7$ particles total) and were able to detect infection in an RNA sample corresponding to $6.65 \times 10^4$ cells from the culture harvested at 4 h p.i. RT and nested PCR are required to detect E1*I,E2 RNAs at this time point and we determined a sensitivity of ~10 targets per reaction. If it is assumed there were 10 targets (E1*I,E2 RNAs) in the $6.65 \times 10^4$ cells, this could equal a range of 1-10 infected cells.

Out of the input 20 particles per cell, $1.33 \times 10^6$ particles contained a maximum of 10 infectious units (P/I≈$10^5$ to 1). This is a very low proportion of infected cells.

Further studies examined experimental infections with HPV18 and with BPV1. Spliced BPV1 E1^E4 transcripts were detected in HaCaT cells (barely visible at a dose of 1000 VDNA particles per cell), C127 cells and BEK cells, with BEK cell infection being the most efficient. These data demonstrate the abilities to culture epithelial cells from different species, to purify infectious PVs from raft tissues, and to detect various PV infections in various cell types.

There are no reports of obtaining infectious high-risk genital PV types from in vivo lesions, either human or animal. Purification of high risk HPV virions has only been accomplished via laboratory cultivation. Using the methods described, we are able to grow and purify high titers of infectious high-risk genital PV types in vitro following the transfection of PV genomes into HECs.

Although RhPV1 genomes replicate in HECs and HPV31b may infect Rhesus monkeys, PVs are generally known to have narrow host range for a complete permissive life cycle. Thus, the detection of RhPV1 early replication (increased life span) and transcription activities in human cells may not ultimately give rise to a complete productive replication cycle resulting in virion production. Thus one approach is to extend the RhPV1 transfections to Rhesus genital epithelial cells (RGECs) as well as to study RhPV1 replication in the HECs to determine whether RhPV1 virions can be purified from these raft tissues as well.

EXAMPLE 6

RhPV1 Genome Transfection and Selection of Stable RGEC-RhPV Lines

Foreskin and cervical tissues from Rhesus monkeys were adapted into primary and secondary cultures using standard techniques, and numerous frozen stocks were made. These cells are grown for approximately 12-18 population doublings by co-culture with mitomycin C-treated J2 3T3 fibroblast feeder cells.

Figure 4A:
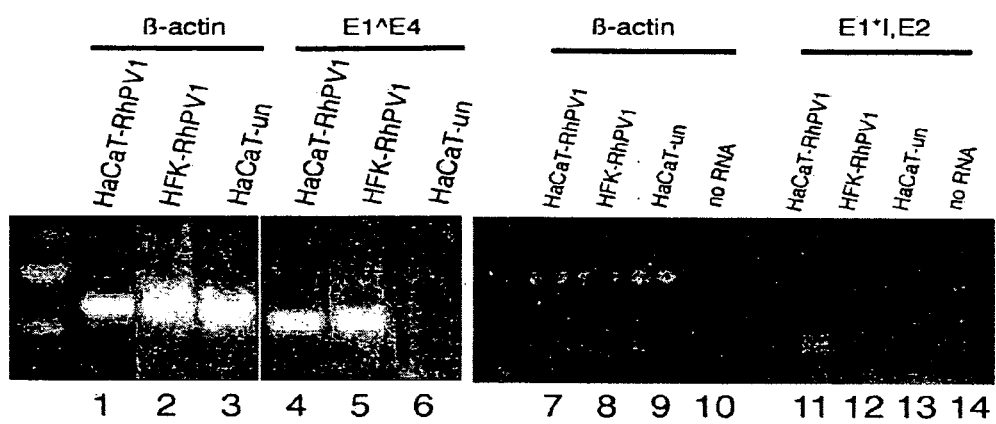
FIG. 4A shows the results of RT-PCR for RhPV1 transcripts in transfected low passage RGEC and low passage HFKs. Cells were transfected with RhPV1 genomes that were excised from the plasmid vector and recircularized. Untransfected cells served as a negative control. The cells were harvested 48 h after transfection for total RNAs. DNase 1-treated, total RNAs were subjected to RT. The cDNAs were divided into aliquots for PCR amplification with primers specific for the spliced products as indicated: RhPV1 E1^E4 (544 bp), RhPV1 E1*I-E2 (407 bp), RhPV1 E6* (239 bp), and cellular β-actin (649 bp) as a control for RT. The products were analyzed by 2% agarose gel electrophoresis. RhPV1 cDNA amplicons were cloned and sequenced or directly sequenced and the cDNA structures are shown in FIG. 4B, viral RNAs A, B, and D.
Figure 4B:
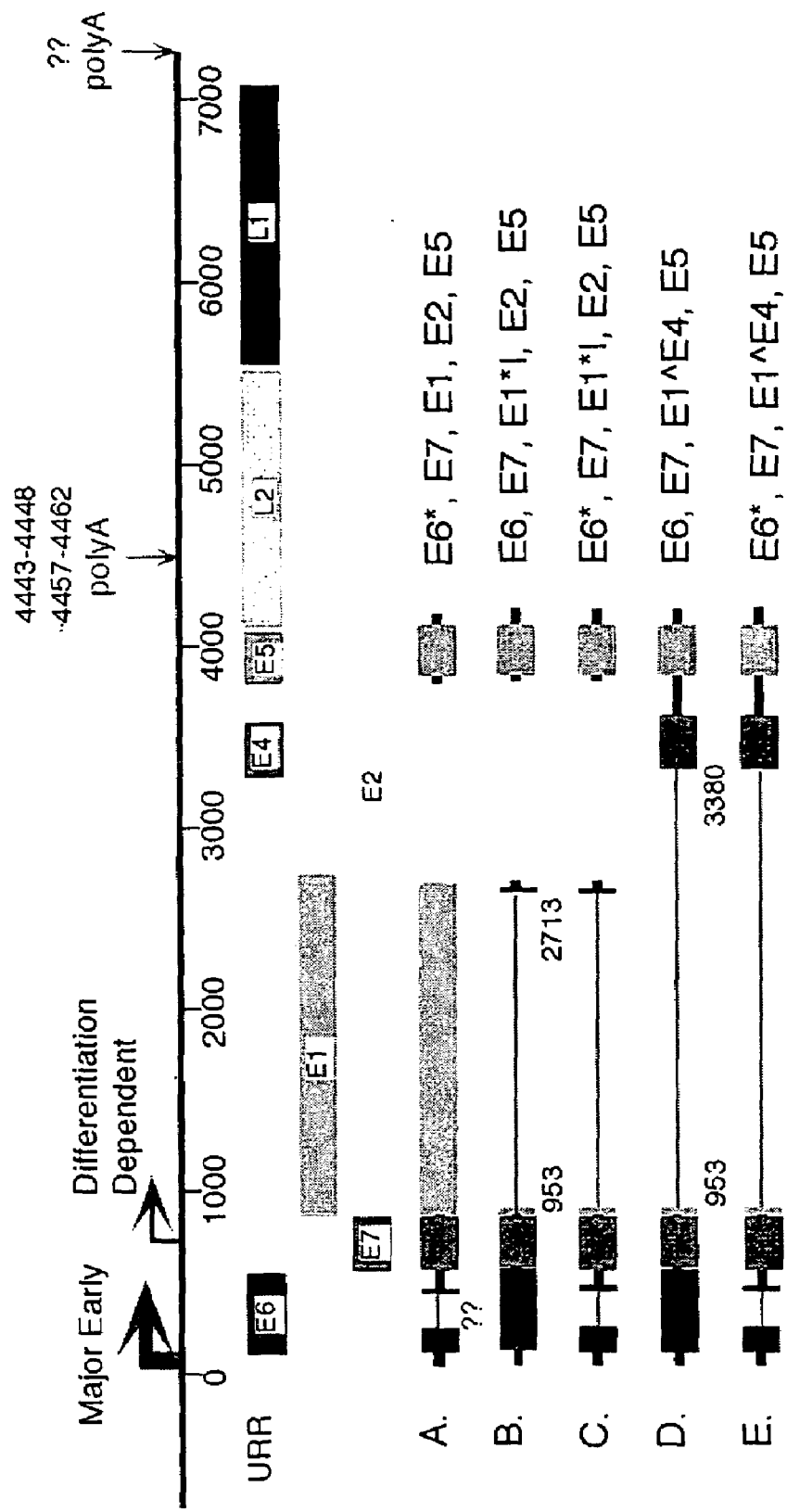
FIG. 4B diagrammatically illustrates RhPV1 genome organization and polycistronic transcripts. The circular RhPV1 genome of 8026 bp is shown linearized at the putative late polyadenylation (polyA) signal to illustrate the ORFs and the RNAs. The nucleotide numbering of the viral genome is given below the thin horizontal rule [60]. Putative promoters are shown by bent arrows; the largest arrow indicates the major early promoter and the smaller arrow indicates the differentiation-inducible promoter found in high-risk HPV types (17-20). The downward arrows mark potential polyA sites. The boxes illustrate the ORFs contained within the polycistronic transcripts (A-E); thick black lines represent noncoding sequences. Thin lines show regions spliced out of transcripts (introns); the shown splice site nucleotides indicated below the transcripts were determined by sequencing RT-PCR amplicons corresponding to RhPV1 E6* (A), E1*I-E2 (B) and E1^E4 (D) derived from transfected human keratinocytes and RGEC cells (shown in FIG. 4A, lanes 11-12 and 4-5, respectively). The regions and ORFs contained in each mRNA are indicated to the right side of each. Other putative transcripts are based upon high-risk HPV types.

We have used the cloned RhPV1 genome to study viral replication. The viral genome is inserted into the plasmid in the late region of the viral genome. The RhPV1 genome was released from the plasmid by restriction digestion, diluted to promote intra-molecular DNA ligation, and recircularized using DNA ligase. The RhPV1 genome was transfected into two human cell lines, HaCaT adult skin keratinocytes and human foreskin keratinocytes (HFKs). DH51C, R377C, and DC55C were also transfected. Transfection was performed using FuGene Lipid Transfection Reagent (Roche) in 6 well plates with $5 \times 10^5$ cells per well. Cell strains were each transfected with 3 μg of RhPV1 genome. RNA was extracted using TRIzol reagent 48 hours post transfection, and 1 μg of DNA-free RNA was subjected to reverse transcription (RT) using random hexamer primers. The RT reactions were then divided into four aliquots and subjected to polymerase chain reaction (PCR) using specific primer pairs specific to the RhPV1 sequence (FIG. 4A). FIG. 4B transcripts A, B and D illustrates the splice junctions that were identified.

The primers that recognize the E6* splice junction amplify a 239 bp product. The splice donor site is AG/GT (located at nucleotide 234) and splice acceptor site is AG/AA (at nt 433). This has been confirmed in at least 3 separate sequencing experiments from each cell line. It is very important to note that this E6* spliced RNA, unlike those for other highly related human papillomavirus oncogenic viruses (HPV16, 18, 31, etc.), does not result in the E6 open reading frame shifting reading frames and terminating translation. Instead, the E6 ORF is maintained. This is striking because the theory for high risk HPVs is that the E6* ORF, with its truncated reading frame due to the frame shift after the splice acceptor, is essential for ribosome re-initiation on the close E7 AUG. However, in RhPV1, an oncogenic high-risk PV, the termination codon from E6 or E6* (the same codon for both) is very close to the E7 ORF, and it is predicted not to allow re-initiation of translation on the E7 ORF. This surprising recognition that the E6 splicing properties are different for RhPV1, a Rhesus macaque PV associated with anogenital cancers, shifts the paradigm for the association of the E6* function in oncogenic viruses.

The E1*I-E2 transcript (product of 407 bp) was also detected in all 4 cell lines after transfection. The splice donor site for E1*I-E2 is AG/GT at nt 953 and the splice acceptor is AG/GA at nt 2713. The E1^E4 RNA (544 bp) was detected, and contains the splice donor site AG/GT at nt 953 and a splice acceptor AG/CG at nt 3380. The E1*I-E2 and E1^E4 transcripts are similar to those mapped for HPV16, 18, and 31.

We have characterized the ability of the RhPV1 genome to replicate in human keratinocytes and RGEC. A crucial part of this invention is the ability to obtain cell lines that maintain stably replicating RhPV1 genomes. This is dependent upon the ability of the cloned genome to replicate upon introduction into cell. We have used the cloned RhPV1 genome to study viral replication. The viral genome was recircularized and transfected into cells as described above using FuGene Lipid Reagent. Cells were harvested for a transient replication assay on days 2, 4, 6, 8, and 10 post transfection by rinsing once with phosphate buffered saline. The cells were released using trypsin, then were pelleted, rinsed with PBS and allowed to dry in a 1.5 ml microfuge tube. The samples were subjected to a modified Hirt DNA extraction protocol to preferentially obtain the low molecular weight DNA from the cells. The cells were resuspended in 250 ul Resuspension solution (50 mM Tris-HCL pH 7.5, 10 mM EDTA containing 100 μg/mL RNase A) followed by addition of 250 μl Lysis solution (1.2% SDS). Following a 5 min incubation at room temperature, 350 ul of Precipitation solution (3M CsCl, 1M KOAc, 0.67M Acetic Acid) was added and samples were placed on ice for 15 minutes followed by centrifugation at 4° C. for 15 minutes at 14000×g. The supernatant was then loaded onto a QIAprep spin column and centrifuged for 60 s. The column was washed with 750 μl of buffer (80 mM KOAc, 10 mM Tris-HCl pH 7.5, 40 uM EDTA, 60% EtOH) and pelleted by centrifugation for 60 s. The low molecular weight DNA was eluted from the column by adding 50 μl water and with centrifugation for 60 s. In the assay showing replication in R377 cells (FIG. 2A) one half of this DNA eluate was subjected to digest with Dpn I and Xho I. The enzyme Dpn I recognizes methylated DNA from bacterial cells and digests all the original transfected DNA, leaving only the DNA that has replicated in the eukayotic cells. The enzyme Xho I linearizes the RhPV1 genome so that it runs at ≈8 kb along side of the copy number controls on the gel. The samples were run on a 0.8% agarose gel and transferred to a nitrocellulose membrane and hybridized with a radioactively labeled RhPV1 DNA probe. The blots were analyzed by exposure to film. The data show that the RhPV1 genome is capable of replicating extrachomasomally in the RGEC. The fact that we can detect and characterize viral transcripts and can detect RhPV1 genome replication in the RGEC in vitro is supportive of the idea that we will obtain RGEC lines that can stably maintain extrachromosomal viral genomes. This allows the growth of raft tissues for the production of RhPV1 virions and the use of the Rhesus monkey model for cervical and anogenital carcinogenesis.

TABLE 1

Oligonucleotide primers used to characterize RhPV1 transcripts

| Name | Sequence (5' -> 3')[a] | Sense or antisense | Nucleotide position[a] | ORF[b] |
|---|---|---|---|---|
| E6A | 5'-AAG GCA AGC CAT ACGGG-3' (SEQ ID NO:1) | sense | 278-294 | E6 |
| E7A | 5'-GGC CTA AAC CTA CCCTC-3' (SEQ ID NO:2) | sense | 600-617 | E7 |
| E7.2A | 5'-CAG CAT CAT CAG CAC GCC-3' (SEQ ID NO:3) | sense | 744--761 | E7 |
| E7B | 5'-GTC TGG CGT GCT GATGAT GC-3' (SEQ ID NO:4) | antisense | 746-765 | E7 |
| E7.3A | 5'-AGT AGC CAC GAA GAGTTA CG-3' (SEQ ID NO:5) | sense | 849-868 | E7 |
| E2B | 5'-CAA GTG CTT CCA TCATTT TCC G-3' (SEQ ID NO:6) | antisense | 2751-2772 | E2 |
| E4.2B | 5'-CAC CTG AGT CTG ACC GAC-3' (SEQ ID NO:7) | antisense | 3508-3525 | E4 |
| E4B | 5'-CAC AAA GGA CTG ACCGGC-3' (SEQ ID NO:8) | antisense | 3556-3573 | E4 |
| L1B | 5'-GCT AGT GCA TAT GTCTAT AGG AAC-3' (SEQ ID NO:9) | antisense | 6495-6519 | L1 |
| β-actin OA | 5'-GAT GAC CCA GAT CATGTT TG-3' (SEQ ID NO:10) | sense | 1578-1587/ 2029-2039 | β-actin |
| β-actin IA | 5'-AAC ACC CCA GCC ATGTAC GTT G-3' (SEQ ID NO:11) | sense | 2046-2067 | β-actin |
| β-actin IB | 5'-ACT CCA TGC CCA GGAAGG AAG G-3' (SEQ ID NO:12) | antisense | 2455-2467/ 2563-2570 | β-actin |
| β-actin OB | 5'-GGA GCA ATG ATC TTGATC TTC-3' (SEQ ID NO:13) | antisense | 2735-2744/ 2857-2867 | β-actin |

[a]corresponding to the sequence and numbering of RhPV1 or spliced human β-actin transcripts.
[b]open reading frame or region of specified gene

EXAMPLE 7

Viral Transcription and Genome Replication Activities in Persistently RhPV1-Infected Cell Lines and Differentiating Epithelial Tissues RhPV1 transcriptional activities and the maintenance and amplification of VDNA in infected tissues can be determined. These data are important to reveal viral activities to target for studies of pathogenesis in vivo in Rhesus macaques. A clonal RGEC-RhPV cell line that contains an average of 50 episomal RhPV1 copies per cell in undifferentiated monolayer culture and that produces infectious RhPV1 virions in the raft system can be employed. Studies are modeled after those of the CIN-612 9E cell line, which contains an average of 50 episomal HPV31 copies per cell in monolayer culture. Based on results to date and without wishing to be bound by any particular theory, it is believed that temporal RhPV1 splicing patterns and promoter usage are similar to those defined for high-risk HPV31. Further, it is believed that during raft epithelial tissue differentiation, spliced RhPV1 RNA levels and vDNA amplification peak about two weeks after lifting to the air-liquid interface and that virion production is maximal at that time.

EXAMPLE 8

Analyses of Viral RNA Structures and Viral Promoters in an RGEC-RhPV Cell Line RT-PCR techniques can be used to investigate viral RNA structures, ribonuclease protection assays (RPAs) to study the temporal expression patterns of specific viral RNAs, and primer extension reactions to determine temporal usage of viral promoters in a manner similar to that reported for HPV31. DNA-free total RNA will be extracted from RGEC-RhPV cells grown as undifferentiated monolayer cultures and as differentiating raft tissues harvested at 4, 8, 12, and 16 days after lifting to the air-liquid interface. Up to about 20 µg of total RNA will be used to perform thorough RT-PCR characterizations from each time point (monolayers, and rafts at 4d, 8d, 12d, 16d). For RPAs targeting early viral RNAs, up to 5-10 µg for each of the seven early viral RNAs at each time point will be employed. Preliminary work showed that cellular cyclophilin RNA is the best internal control to use for quantification of RNAs expressed in undifferentiated and raft differentiated HECs. Two novel spliced RhPV1 transcripts have been defined by RT-PCR and sequencing, E1*E2 and E1^E4, and are structurally similar to those expressed by HPV16 and HPV31. These similarities include conservations of a splice donor in the 5' end of the E1 ORF (at nt 953) that is used to supply a start codon for the E4 ORF and is used to splice for E2 RNAs; a splice acceptor in the E4 ORF (at nt 3380) that maintains the reading frame with E1; and a splice acceptor upstream of the E2 ORF (at nt 2713). Spliced transcripts analogous to those found in HPV31 infected rafts and monolayers can be detected and characterized, as well as a major early promoter upstream of E6 and a differentiation-inducible promoter in the E7 ORF.

EXAMPLE 9

Analyses of vDNA in RGEC-RhPV Cell Lines

Total DNA is extracted from RGEC-RhPV cells grown as undifferentiated monolayer cultures and as differentiating raft tissues harvested at 2, 4, 6, 8, 10, 12, 14, and 16 days after lifting to the air-liquid interface. Raft tissues are harvested at these time points for paraffin embedding and histological sectioning. One approach is to use DNA extraction and Southern blot hybridizations to analyze the episomality and levels of VDNA in the undifferentiated cells and differentiating raft tissues as reported for HPV31. These experiments will give data on the average copy number of vDNA per cell and will show the temporal, differentiation-induced amplification of vDNA. In situ hybridization is performed in raft tissue sections to visualize the individual cells undergoing vegetative vDNA amplification during differentiation. Thus the time point at which stage III vDNA replication occurs during the differentiation of RGEC-RhPV raft tissues can be determined. vDNA amplification can be correlated with the temporal expression levels of the transcripts for the viral replication E1 and E2 proteins.

EXAMPLE 10

Viral Transcription Activities in Newly Infected Low Passage Rhesus Monkey Genital Epithelial Cells In Vitro The early stages of PV gene expression and genome replication following the infection of epithelial cells in vitro is studied. Viral RNA expression has been detected following the infection of cultured epithelial cells with stocks of CRPV, HPV1, HPV11, HPV16, and HPV18. We were the first to examine the usage of viral promoters following experimental infections. We observed differences in viral mRNA splicing in HPV18-infected monolayer foreskin HECs at 24-h p.i. compared with those harvested at 72-h p.i. and later. The HPV31 $P_{7783}$ and $P_{7855}$ promoters are negatively regulated by differentiation, suggesting that they may be important early in infection. Temporally, regulated induction of spliced E6, E1, E2, E8^E2C, and E1^E4 transcripts were observed upon HPV31 infection of HaCaT cells, and seven novel spliced HPV31 RNAs were characterized. These data suggest that a promoter other than the major early promoter ($P_{99}$) is used for the initiation of E1^E2 transcripts or that differential splicing is occurring very early in infection. HPV31 studies showing induction of differentially spliced viral RNAs suggests that there is a rather abrupt and steep rise in viral RNA expression following infection providing further justification for these experiments. RhPV1 viral RNA structures and viral promoters following experimental infection of RGECs can thus be temporally characterized. The hypothesis is that qualitative and quantitative changes in RhPV1 splicing patterns and promoter usage will be observed from initial infection to 24 h p.i., just as occur in newly HPV31-infected cells. Further, we theorize that these changes will indicate gene products, possibly novel proteins, important at early stages of high-risk PV infection. Additionally, early measures of RhPV1 transcripts may be relevant or predictive of subsequent outcomes of infection in vivo. Characterization of viral immediate early promoters may also reveal cellular proteins that can be targeted to prevent infection.

EXAMPLE 11

Analyses of Viral RNA Structures by RT-PCR

Subconfluent RGEC monolayers are inoculated with serially diluted doses of 1000, 100, 10 and 1.0 RhPV1 vDNA-containing particles per cell with mock infections serving as negative controls. None of the PVs tested in infectivity assays have required a dose larger than 100 vDNA-containing particles per normal host cell for efficient infection detection. Harvesting at 4 d p.i., HPV31 infection can be detected at a dose as low as 1.0 vDNA particle per cell in HECS and BPV1 infection can be detected at a dose as low as 10 vDNA particles per cell in bovine epithelial keratinocytes (BEK). HPV31 infections using a dose of 10-20 vDNA containing particles per cell are detectable by RT-PCR as early as 4 h p.i. Similar infectivity efficiencies can be determined for RhPV1 in RGEC. RGECs will be infected as described for HPV31. DNA-free, total RNAs will be harvested at 2-h time points from 2 to 24 h p.i. Total RNAs from persistently infected RGEC-RhPV cells will be used as positive controls for RT-PCR. The major advantage of RT-PCR-based analyses is the sensitivity and this is important since we seem to have a small percentage of the cells infected.

EXAMPLE 12

Quantification of Temporal Viral RNA Expression by RPAs

RPAs are employed to complement the RT-PCR studies. RPAs are more specific and are used to confirm temporal quantitative differences in viral RNA expression as indicated by RT-PCR. In addition, multiple viral RNAs can be assayed in a single sample, provided the protected RNAs can be distinguished by electrophoretic size in a polyacrylamide gel. However, RPAs are less sensitive than RT-PCR and for HPV31 infections doses of 10-100 virions per cell are required to detect viral RNAs by RPA. As stated above, 5-10 µg of total RNA is needed for an RNase protection for detection of HPV31 early genes in CIN-612 9E cells. As ≈20 µg of total RNA is obtained from 6-well plates of subconfluent cells, these analyses may require the infection of a larger number of cells. Infection of 60-mm dishes would yield ≈40 µg of total RNA for analysis. Mock infection will serve as a control. The partial RhPV1 cDNAs plus any additionally cloned viral cDNAs obtained are used to make antisense RNA probes for RPAs as previously detailed. Cyclophilin RNA are used as the internal control for quantification of viral RNAs. Time points for analysis are chosen based upon the expression patterns revealed by RT-PCR studies. For example, if a given RNA splicing pattern is found at 12 h but not at 4 or 8 h, then time points are analyzed from 8- to 16-h p.i. with an antisense probe specific for that RNA structure. This defines the onset and/or subsidence of expression of specific RhPV1 transcripts, providing information on the importance of the transcript in early vDNA replication. Thus the initial expression times of specific viral transcripts are defined, and their temporal expression patterns during these early phases of RhPV1 infection are followed.

EXAMPLE 13

Temporal Quantification of HPV Promoter Usage by Primer Extension Assays or 5' Rapid Amplification of cDNA Ends (5'-RACE)

The temporal expression from eight HPV31 promoters using primer extension analyses on total RNAs from CIN-612 9E cells and raft tissues have been precisely mapped and defined. Multiple RhPV1 promoters are characterized, and analysis of the initial stages of RhPV1 infection may reveal additional promoters important in the early stages of the viral life cycle. In addition to testing for promoter analogous to the eight known HPV31 promoters, RhPV1 promoter(s) upstream of the E1 and E2 ORFs are specifically assayed. HPV types 6 and 11 utilize a differentiation-dependent promoter in the E7 ORF to initiate a subset of E1 ORF-containing transcripts. The analogous promoter in HPV31b is $P_{742}$. Use of these promoters early in infection for initiation of E1-, E1^E2-, and E2-specific transcripts is determined. The time points of harvest for these analyses are chosen based upon the data from RT-PCR and/or RPAs showing greatest expression of specific transcripts/ORFs. This maximizes the sensitivity of the assay. Where there is evidence for novel promoters early in infection, 5'-RACE PCR techniques are used to investigate the 5' ends of the RNAs.

EXAMPLE 14

Infection in Rhesus Macaques

Infection in Rhesus macaques is analyzed. In vivo experimental infections permit essential investigations into the pathogenesis of genital PV infections. This model allows the study of the natural history of genital PV infections including animal-to-animal transmission, cellular immunology, acute and chronic pathology (neoplasia), and malignant progression. Infected animals are followed for periods up to three to five years to determine whether and how the infections resolve, as they are believed to do, in the majority of human cases. This also yields a small group of animals that have progressively more neoplastic and malignant lesions. Co-infections with SIV1 permit the study of molecular aspects of these PV infections in the context of AIDS. Molecular viral and cellular mechanisms that control the establishment of genital PV infections with a potential for malignant progression are thus better defined. Using the present Rhesus model system, prophylactic and therapeutic agents can be evaluated for efficacy in preventing or treating rhesus as well as human papillomavirus infections and complications thereof, especially anogenital cancers. Characterization of host immunological responses to viral infection and potential prophylactic or therapeutic agents is possible, as well as studying the molecular bases for the effectiveness of such agents. Furthermore, the pathogenesis of mutant viruses created by reverse genetics is studied in this novel animal model.

Rhesus monkeys are handled under general anesthesia per standard primate care guidelines. Ten females are screened 75 days prior to inoculation with RhPV1 virions. Fewer than 40% had been found in previous studies to have been exposed to RHPV. Cervical Pap smears are collected in liquid cytology medium (ThinPrep) suitable for both host and viral DNA and RNA analyses. Anogenital (cervical, vaginal and anal) swabs are placed in separate tubes of HPC Digene standard transport medium (STM; Digene Corporation, Silver Spring, Md.). A cervico-vaginal lavage (CVL) is obtained using 10 mL sterile normal buffered saline. All samples are processed by RhPV1-specific PCT to verify that the animals are not infected with the virus. Ten mL of blood are collected from each animal and assayed for complete blood count andrhPC1-specific antibodies by ELISA to verify that the animals have no RhPV1 antibodies.

Physical examination of the animals including Pap smears, anogenital swabs, CLS and blood draw with their respective PCR and ELISA constitute the core sample of the animals. Three RhPV1-negative females are chosen for these studies. At 14 days prior to inoculation, core sampling is again carried out for each animal. A baseline colposcopy with and without aceto-white staining is performed with cervical photography documentation (cervicography). To establish baseline histology, cervical biopsies are collected in suitable tissue storage medium (for example, RNAlater, Ambion Inc., Austin, Tex.). This reagent permits the same sample to be used for histological sectioning and for nucleic acid isolation.

On day 0, core sampling is again repeated. The vaginal and cervical areas are dried with cotton swabs and the cervical opening and transition zone is denuded with a cervical brush to expose the basal cells. RhPV1 virions are inoculated onto the cervix in 0.5 to 1.0 mL total volume ($10^9$ viral DNA-containing particles per animal). The animals are maintained with their knees up for 30 min to help keep the inoculum in place.

At 2 and 4 months after inoculation, core samplings are performed. Additionally, at 4 months p.i., colposcopy with and without aceto-white staining and cervicography are performed on each cervix to reveal any areas of abnormality. All abnormal areas are biopsied and stored in the RNAlater tissue storage medium. At 6, 8 and 12 months after infection, sample and examinations are performed as at 4 months p.i. If no areas appear abnormal, two random biopsies are taken at 6 and 12 months p.i. If at 12 months p.i. evidence for infection is weak, or if there is strong evidence for infection, cervices are obtained by conization. Such cervical tissues and/or additional; abnormal biopsy materials are process for cell culture and further analysis of infection. However, if there is good evidence for infection, then long term evaluation and testing are carried out.

The Pap smears provide pathological evidence of PhPV1 infection by iden6tifying abnormal cells and premalignant lesions that are pathopneumonic for high-risk genital PV infection. Cervical biopsies are frozen, fixed, sectioned and stained with hematoxulin and eosin to observe the architecture of the epithelium and PV-induced changes (e.g., koilocytes) and for RhPV1 vDNA by in situ hybridization. From the CVL and the blood samples, ELISAs are performed for RhPV1-specific antibodies. Blood samples are also analyzed for complete blood count and T cell count. In vaccination studies using large amounts (50-100 µg) of HPV virus-like particles, antibody response was seen by one month p.i. In natural history studies of incident HPV16 infections, seroconversion occurred most frequently between 6 and 12 months after inoculation. RhPV1 antibodies are expected by 6 months p.i. Additional biopsy material and the core samples are processed for DNA and RNA isolation. RhPV1-specific PCR and assay for E1^E4 RNAs (and other viral RNAs shown to be present early after infection). Spliced RNAs are indicative of RhPV1 infection because these RNAs are not present in the challenge virion preparations.

TABLE 2

Genomic RhPV1 sequence (NCIB AC M60184 M37718 (1993).
See also SEQ ID NO:14.

```
FT      CDS          22 . . . 597
FT                   /note="E6 ORF from bp 1 to 597"
FT                   /product="transforming protein"
FT                   /gene="E6"
FT                   /note="putative"
FT                   /codon_start=1
FT      protein_bind 37 . . . 48
FT                   /bound_moiety="E2 protein"
FT                   /note="putative"
FT      protein_bind 52 . . . 63
FT                   /bound_moiety="E2 protein"
FT                   /note="putative"
FT      TATA_signal  67 . . . 71
FT                   /note="putative"
FT      CDS          594 . . . 935
FT                   /note="E7 ORF from bp 582 to 935"
FT                   /product="transforming protein"
FT                   /gene="E7"
FT                   /note="putative"
FT                   /codon_start=1
FT      protein_bind 653 . . . 664
FT                   /bound_moiety="E2 protein"
FT                   /note="putative"
FT      CDS          941 . . . 2818
FT                   /note="E1 ORF from bp 902 to 2818"
FT                   /product="replication protein"
FT                   /gene="E1"
FT                   /note="putative"
FT                   /codon_start=1
FT      polyA_signal 1493 . . . 1498
FT                   /note="putative"
FT      protein_bind 2570 . . . 2581
FT                   /bound_moiety="E2 protein"
FT                   /note="putative"
FT      CDS          2757 . . . 3857
FT                   /note="E2 ORF from bp 2730 to 3857"
FT                   /product="regulatory protein"
FT                   /gene="E2"
FT                   /note="putative"
FT                   /codon_start=1
FT      TATA_signal  2889 . . . 2893
FT                   /note="putative"
FT      TATA_signal  3018 . . . 3022
FT                   /note="putative"
FT      CDS          <3355 . . . 3630
FT                   /note="E4 ORF from bp 3355 to 3630"
FT                   /gene="E4"
FT                   /note="putative"
FT                   /codon_start=1
FT      repeat_region 3857 . . . 3963
FT                   /rpt_unit=3857 . . . 3874, 3946 . . . 3963
FT                   /standard_name="Direct repeat"
FT                   /note="putative"
FT      CDS          <3940 . . . 4413
FT                   /note="E5 ORF from bp 3940 to 4413"
FT                   /gene="E5"
```

TABLE 2-continued

Genomic RhPV1 sequence (NCIB AC M60184 M37718 (1993).
See also SEQ ID NO:14.

```
FT                /note="putative"
FT                /codon_start=1
FT      polyA_signal   4443 . . . 4448
FT                /note="putative"
FT      polyA_signal   4457 . . . 4462
FT                /note="putative"
FT      CDS       4468 . . . 5868
FT                /note="L2 ORF from bp 4462 to 5868"
FT                /product="minor capsid protein"
FT                /gene="L2"
FT                /note="putative"
FT                /codon_start=1
FT      TATA_signal    5122 . . . 5126
FT                /note="putative"
FT      CDS       6289 . . . 7353
FT                /note="L1 ORF from bp 5872 to 7353"
FT                /product="major capsid protein"
FT                /gene="L1"
FT                /note="putative"
FT                /codon_start=1
FT      TATA_signal    6904 . . . 6908
FT                /note="putative"
FT      protein_bind   7670 . . . 7681
FT                /bound_moiety="E2 protein"
FT                /note="putative"
FT      protein_bind   7845 . . . 7859
FT                /bound_moiety="hormone receptor"
FT                /standard_name="glucocorticoid responsive element"
FT                /note="putative"
FT      protein_bind   7986 . . . 7997
FT                /bound_moiety="E2 protein"
FT                /note="putative"
```

```
tacttaacta  tactcctgag  tatgaaaaag  ggtgtaaccg  aaaacggtgc  aaccgaaagc    60
ggtgcatata  aaaagctcct  gaaactttgg  ttttttgtgg  caatggtaga  ctgccctggc   120
gagccaaacg  aattgcccag  gaccattcac  gaactatgcg  agcagcgtga  ggagaccctg   180
cacgagcttc  aattggagtg  cgtgtattgc  ctgaaggaac  taacacgcat  tgaggtatat   240
gattttgcac  ggtgggattt  aagattggtg  catagacaag  gcaagccata  cggggtatgt   300
cccatatgct  tgaggtttta  ctcaaaaatt  cgaaaatata  ggcgatacga  gtattcaata   360
tatgggtgta  ctttagagcg  tagaactaga  aaacagttag  tggaggtatt  aataaggtgt   420
tattgttgtc  agaagccct   gtgtcccatt  gaaaagcaaa  gacacgtgga  ccaaggacaa   480
aggttccaca  gaatagcggg  acagtggacc  ggaaggtgct  tgatgtgctg  gagaccaaca   540
gtacctgaga  cccagccaga  cactgatcaa  cagggcagta  gtttcttgca  agcatgattg   600
ggcctaaacc  taccctcgag  gacattgtcc  tagatttgca  accatttcca  caaccgcaac   660
cggtcgacct  tatgtgttat  gagcaattat  ctgacagctc  agaggatgag  gatgaagtag   720
accatcatca  caataatcag  cagcagcatc  atcagcacgc  cagacctgaa  gtaccagagg   780
atggtgattg  ttatagaatt  gtgagcgatt  gttacagctg  tggcaagcca  ctgaggctgg   840
ttgtggttag  tagccacgaa  gagttacgtg  tgctagagga  cctgctgatg  ggcacgcttg   900
acattgtgtg  tcccagctgt  gccagcagag  tgtaactgca  atggaccctg  aaggtacacc   960
aggggaaggg  gtgggtgta   cggggtggtt  taatgtggag  gctatagtag  aacgtaaaac  1020
gggggatgtg  gtgtcagagg  acgaagacga  cacagaggat  acagggatag  atttggtaga  1080
ctttatagat  gacacatgtg  gaagtgtgca  gacagggac   gaggcacctg  gggcgttgtt  1140
gcacgcacag  gaaacacaag  cgcatgcaga  ggcagtgcag  gttttaaaac  gaaagtttgt  1200
aggcagtccg  gcagttagtc  cgttgggaaa  ctacaatccc  tgtgtagaca  gggatttaag  1260
tcccagatta  aatgaaataa  gtttaaacca  aggcagcgga  caggcaaaac  ggagactgtt  1320
```

TABLE 2-continued

Genomic RhPV1 sequence (NCIB AC M60184 M37718 (1993).
See also SEQ ID NO:14.

| | | | | | | |
|---|---|---|---|---|---|---|
| tttgccggac | agcggttatg | gcaatactga | agtggaaacg | tcgctattgc | aggtagcagg | 1380 |
| gggggcggc | caggatgtac | aggcagggg | gaaggaaaac | acacggccag | atgacggggg | 1440 |
| ggggatgcc | acgcagctgc | tccgttgcag | caacttaaaa | gccactttgc | tgagtaaatt | 1500 |
| taaatctgtg | tatggagtta | gcttttcaga | gttggtgcga | agctttaaaa | gcgacaggac | 1560 |
| cacgtgcgct | gactgggtgg | tggggcagc | ggggtccat | catagcgtgg | cagagggtt | 1620 |
| aaagcagctc | attcagcctt | tttgcagtta | tgcacacatc | cagtgcctta | catgcgactg | 1680 |
| ggggtgtac | ctgctactgc | tggcacggtt | taagtgtggc | aaaaacagac | taacagtttc | 1740 |
| taaatgcatg | agcacgctgt | taaatgtgca | agaaacgcac | atgctaattg | aaccaccgaa | 1800 |
| gctgcgtagc | gcagcagcag | ctctatactg | gtacaggaca | ggtatatcaa | atgtaagtga | 1860 |
| agtaataggg | gaaacacctg | agtggattac | aagacagaca | atgtttcaac | atggcctgga | 1920 |
| ggacagtata | tttgatttgt | ctgaaatggt | gcagtgggca | tacgaccacg | actttacaga | 1980 |
| tgacagtgtg | atagcgtacg | agtatgcaca | gctggcaggg | atagacagca | acgctgctgc | 2040 |
| attttttaaaa | agtaatgcac | aggccaaata | tgtgaaggat | tgtgccacta | tgtgtaggca | 2100 |
| ctacaaaaga | gccgaaaggc | aacagatgac | tatgtcacag | tggataaaac | aaggtgtga | 2160 |
| aaaaactgat | gatggagggg | actggaggcc | aatagtgcag | tttttaaggt | accaagggt | 2220 |
| ggagtttata | gcattttag | cagctttaaa | gctgttttg | aagggcattc | caaaaaaaaa | 2280 |
| ctgcatagtg | ttatttggac | cgccaaatac | aggtaaatcc | tactttggca | tgagcttaat | 2340 |
| acatttcttg | caagggtcta | tcatttcata | tgtaaattcc | aacagtcact | tttggttgca | 2400 |
| gcctctggca | gatgctaagg | tggccatgtt | ggatgatgca | actcctcagt | gctggtccta | 2460 |
| tatagataat | tatttaagga | acgcactgga | cgggaaccc | attagtgttg | atagaaaaca | 2520 |
| taaaaatctt | gtacagatga | agtgccccc | attgcttatt | acctcaaaca | ccaatgcagg | 2580 |
| tcaggatgac | aggtggatgt | atttgcacag | tagaatggtt | gtgtttacat | ttgaacagcc | 2640 |
| atttccatt | gatcagaacg | gtaatccagt | ttatgagtta | aatgataaaa | actggaaatc | 2700 |
| cttttttctca | aggacatggt | ccagattaga | tttacaagag | gaagaggaga | cggaaaatga | 2760 |
| tggaagcact | tgcagagcgt | ttaagtgcgt | tgcaggacag | aatcttagaa | ctgtatgaag | 2820 |
| ctgatagcaa | ggacttaaaa | gaccaaatag | agcactggaa | atgtgtgcgc | caagaatgtg | 2880 |
| cagtgttgta | taaggcacgg | gaagtagggt | tttcccacct | gaaccatcag | gtggtgccat | 2940 |
| cattaactgt | gtcacgggct | aaagcccaca | aagcaattga | agtgcagctg | gcattagaga | 3000 |
| gtttacaaaa | ttcggagtat | aacaatgagg | agtggacgct | gcaagatgcc | agcttggaga | 3060 |
| tgtggcacac | agaacctaag | ggatgcttca | aaaaaacagg | tgttccagta | acagttttgt | 3120 |
| ttgactgtga | caaagacaat | accatggagt | atgtgctgtg | gggacacata | tatgtgtggg | 3180 |
| gggacaatgg | atgggtgaag | acattcggtg | aggcggacaa | ctgggtctg | cactataccg | 3240 |
| ttgctgggga | aaaggtgtac | tatgtgcagt | tttatgagga | tgctaaaaaa | tatggacatg | 3300 |
| gaaatggaaa | tggagatggc | tatgagtggg | aggtgcatgt | tggtgggacg | gtaatgcatt | 3360 |
| attctgactc | tgtgtctagc | gctacccact | gcgacaaact | acccactgtt | gaaattgtta | 3420 |
| gcggactgca | acacatcaac | ccatcacccc | ccccgccaa | ccccagcgcc | aaggaaaacg | 3480 |
| tgtggtcatc | gcctgcaaag | cgagtgcgtc | ggtcagactc | aggtggagat | ccagtgcggg | 3540 |
| ccttggacgg | taaaagccgg | tcagtccttt | gtggatctgc | acacaacaac | gctacaggga | 3600 |

TABLE 2-continued

Genomic RhPV1 sequence (NCIB AC M60184 M37718 (1993).
See also SEQ ID NO:14.

| | | | | | |
|---|---|---|---|---|---|
| gttccggtga | cagtgactat | acgcctatag | tgcacctaaa | aggtgaatct | aactgtttga 3660 |
| agtgtttgcg | gttcagactg | ggaaagcata | agcacctgta | tattaatata | tcgtccacct 3720 |
| ggaggtgggc | aaaccatgca | agtgagaaag | caattgtaac | tgtgacattt | gcaaatgagc 3780 |
| ttcaaagaca | acagttttta | aacactgtaa | aaataccttc | tactgtaact | ctgtcacaag 3840 |
| gagtaatgac | tgtgtagtgt | gcattggcac | acagggtttt | gtattttttt | ttttacaagt 3900 |
| actgtttgta | attaattttg | tatattgact | gtatattgaa | ttgtggtgtg | cattggcaca 3960 |
| cagtggtctc | atttcaagcc | tgtacataca | ttgaacagta | tccaggtact | gtgtaaagcc 4020 |
| aattgttgct | gctacgcttg | taaaccgcca | ccattctgct | gtttctggtt | gtgttttgc 4080 |
| tgctgttttt | gcttggcctt | gtgttttgtg | cacttgttga | gtcgctgctt | ctgtgttttt 4140 |
| ccggtatgcc | tcagtgttgc | tgcttatgct | gttgttctgg | gtgtccatag | tgaacccgtt 4200 |
| tgcagctttt | ggtctgtgtt | tgttttgttt | tttaaccccg | ttgcttttga | tacacctgca 4260 |
| tgccctcagt | gtggtttaca | gcagaatgat | gtaaatactg | cacatagaca | tgttattatc 4320 |
| agttattttg | ctattgttgc | tgttaatatt | tactttgttt | tggcactact | tgttggtgct 4380 |
| gcgtttaaag | ccaccagcag | ggcgcgcacg | taaatgtaaa | cagctgagac | ggcggcgcag 4440 |
| ataataaacg | tcacacaata | aagcgtcatg | aagcatgcac | acttgtcgcg | gcgcaagcga 4500 |
| gcagccccgc | gcccacctgg | tgggcggcaa | aagcgtgcat | ctgccacgca | gctgtaccaa 4560 |
| acctgcaagg | cggcaggcac | atgcccccc | gatgttatcc | ctaaggtgga | aggcacaacc 4620 |
| gtagcagatc | aaattttaaa | gtatgcgagc | atgggtgtat | actttggggg | tttgggcatt 4680 |
| ggctctggtg | ctggcacggg | cggaagaagc | ggctacgtgc | ccctaggttc | acgtcccgca 4740 |
| tccattcccg | agccgttgcc | acgaccacca | gtaacaattg | agcctgtggg | cccttccgat 4800 |
| ccctccattg | tgtcattgct | ggaagagtcc | agactaatag | aggcaggtgt | tccagccccc 4860 |
| acattcccca | ctcatggggg | gtttgaaatt | agcacatctg | aagttagcac | acccgctgtc 4920 |
| ctggatgtgt | ctagcggtgg | ctctgatgtg | cacgttagtg | tgacctcctt | tacaaaccct 4980 |
| accttactg | agccatctgt | gctgcgaccc | ccgcccccg | tagaggcgtc | tggacgcctg 5040 |
| gtaatctctg | catcctctgt | cagcacgcat | agctacgaag | aaatacccat | ggacacattt 5100 |
| gtaataactg | gagaccacaa | ctataacaca | accagcacac | ccattcctgg | ttcacgtgcc 5160 |
| cctgcacgac | ttggtctata | tggacgtgct | acccagcaag | tgcgggtggt | ggatcctgca 5220 |
| tttataacca | cccctgcgcg | actggtgaca | tatgacaacc | ctgcatatga | gggtgtggac 5280 |
| gatgccaccc | tgcaattttc | ccactctgac | attcaccagc | cgccagatcc | tgacttcctt 5340 |
| gacattgtgg | cattgcacag | gcccgccttg | acctcacgta | agggcaccgt | gcgctttagc 5400 |
| cgattaggcc | agcgggcaac | actaaccacg | cgcagtggta | agcgtattgg | ggccaaggtg 5460 |
| catttctatc | atgacctcag | tcccattgcc | cctgcagaaa | gcatcgagtt | gcagcccctg 5520 |
| tcatctcagg | gagagctgta | tgacatatat | gcagatgtag | acgggcaaga | ggacgctgca 5580 |
| gctgtggcta | acaccccatt | aaacagcaac | agcagtggca | ttgcaagccc | ctggaacacc 5640 |
| acagtgccac | tcagtgcagg | ggcggacgtg | acgctgcagt | ccggccccga | cgtgtccctg 5700 |
| gatgcaccag | tggctgaatc | gcctgtgcac | cctggagtgc | ctctaaggcc | ttctgcacat 5760 |
| attattctgt | acgggggaga | ctttttatttg | caccctagct | acctcggtat | tcgcaggaaa 5820 |
| cgtaaacgca | tgcacaattt | cttttcagat | gtctatgtgg | cggcctagtg | actccaaggt 5880 |

TABLE 2-continued

Genomic RhPV1 sequence (NCIB AC M60184 M37718 (1993).
See also SEQ ID NO:14.

| | | | | | |
|---|---|---|---|---|---|
| ctacctacca | cctgtcctgt | gtctaaggtg | gtcagcacgg | atgaatatgt | ctctcgcaca | 5940 |
| agcatatact | atcacgctgg | cagttccaga | cttctggctg | ttggacatcc | ctactatgct | 6000 |
| gtaaagaagg | gcaacaacaa | agtgtcagtg | cccaaggttt | ctggtttaca | ataccgagtg | 6060 |
| tttcgagtgc | gtttgcctga | ccccaataag | tttggccttc | cagatgctaa | cttttatgac | 6120 |
| cctaacacac | agcgccttgt | gtgggcctgt | ttaggcgtgg | aggtggggcg | tggacagcca | 6180 |
| ctgggagtgg | gcaccagtgg | tcatccactg | ctgaacaaac | tagatgacac | ggaaaatggc | 6240 |
| cctaaagtgg | ccgggggaca | aggagcagat | aacagggaat | gcgtgtcaat | ggactacaag | 6300 |
| caaacacagc | tgtgcatgct | aggatgcaag | cccctgtgg | gtgagcattg | gggaaaagga | 6360 |
| aatccttgca | ccactggcgc | tgcaggtgac | tgccctgcac | ttgagcttgt | taactcagtt | 6420 |
| atacaggatg | gggacatggt | tgatacaggg | tatggcgcta | tggactttaa | tgcactgcag | 6480 |
| gccaacaaat | cagatgttcc | tatagacata | tgcactagcg | tgtgcaaata | ccctgactat | 6540 |
| ttaaaaatgg | catcagatcc | ctatggcgac | agcttgtttt | tttacctgcg | aagggagcaa | 6600 |
| atgtttgtca | gacacctgtt | taacagagct | ggcacaatgg | gtgacagtgt | ccctgatgac | 6660 |
| ttgtatatta | aaggcagtgg | aagcaatgtc | aagcttgcca | gccacgtgtt | ttaccccaca | 6720 |
| cctagtggct | caatggtgac | atctgatgcc | caattattta | acaagccata | ctggttacag | 6780 |
| aaagcccagg | gccataacaa | tggcatctgt | tggggcaacc | aagtgttcct | tactgtagtt | 6840 |
| gacaccacta | ggagcacaaa | catgacactg | tgtgcatcca | ctgcctccac | agttactaca | 6900 |
| ccatataata | atgagagttt | taaagagtac | ctgcgacatg | tggaggagtt | tgatttgcaa | 6960 |
| tttatatttc | agctgtgcaa | ggtaaccctg | aacactgaag | taatggccta | catacacagc | 7020 |
| atggatgcca | gcatactgga | ggactggaac | tttggttttgc | agcctcctcc | gtctggctcc | 7080 |
| ttgcaggaca | cctataggtt | tgtgacgtct | gccgccatca | cctgtcaaaa | acctgcaccc | 7140 |
| cccaaagaaa | aggaagaccc | gttggctaag | tataccttt | gggaggtgga | tttaaaggaa | 7200 |
| aagttttctg | cagatttaga | ccaatttccc | ttaggccgca | aattttttgct | gcaagctggc | 7260 |
| atgcgtgcac | gccctaccct | gcgcgccccc | aaacgcacag | cctcatctac | ctcatcttcc | 7320 |
| agcccccgca | aacgcaaacg | caccaaacgc | taacgttgct | tatatttatg | ttgttgtacc | 7380 |
| cagtgtgcat | gatttatgta | tgtgtgcatg | ttgtacgtga | ttttgtattt | cctgtgttgt | 7440 |
| gcgtgtcact | gttttgtgtt | gttgcgtgag | tgtgttgcac | ttatgtgttt | attaaagtat | 7500 |
| gcgtggtcgc | acccgagtga | gtaactgtgt | gtgtccggcg | tgtagtttct | gtcacatgca | 7560 |
| tgcatgcaca | cccaaacact | gttgccactg | cctttaacag | cttgcctgct | gcacttccat | 7620 |
| tttgaaccct | tctccattt | ccctgcaaac | cctccatttt | atggtctcga | ccggtttcgg | 7680 |
| tcgcgcttgg | cacgcatttt | gggcaaacaa | aaccacaaca | ctgctaatcc | tctggcttcc | 7740 |
| tgcctctcct | actgctgcat | acctgtggtt | gtgctttggc | gctccctggt | gactcactgt | 7800 |
| ctctgcaaac | aaaaatttgc | acacacactt | aatccaaccc | tctttgtaca | aaatgctttt | 7860 |
| ggcagtacat | ttctaagagt | tactcatgct | aattgcatag | ttggccacaa | tttcagggtt | 7920 |
| ggattgccaa | tactatgtcc | ttttaaatgt | gattaatttt | caaaatgttc | ttgcaggtgt | 7980 |
| gtgtgaccgg | gatcggtcaa | actttcacaa | gcattttta | tagtaa | | 8026 |

//

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference to the extent that there is no inconsistency with the present disclosure.

REFERENCES

1. Boshart, M., L. Gissman, G. Ikenberg, A. Kleinheinz, W. Scheurlen, and H. zur Hausen. 1984. A new type of papillomavirus DNA, its presence in genital cancer biopsies and in cell lines derived from cervical cancer. EMBO J. 3: 1151-1157.
2. Broker, T. R., and M. Botchan. 1986. Papillomaviruses: retrospectives and prospectives. Cancer Cells. 4: 17-36.
3. Chan, S.-Y., H.-U. Bernard, M. Ratterree, T. A. Birkebak, A. J. Faras, and R. S. Ostrow. 1997. Genomic diversity and evolution of papillomaviruses in rhesus monkeys. J. Virol. 71: 4938-4943.
4. de Villiers, E.-M. 1999. 17th International Papillomavirus Conference, Charleston, S.C.
5. de Villiers, E.-M. 1989. Heterogeneity of the human papillomavirus group. J. Virol. 63: 4898-4903.
6. Dürst, M., G. Gissman, H. Ikenberg, and H. zur Hausen. 1983. A papillomavirus DNA from a cervical carcinoma and its prevalence in cancer biopsy samples from different geographic regions. Proc. Natl. Acad. Sci. USA. 80: 3812-3815.
7. Ho, G. Y. F., R. D. Burk, S. Klein, A. S. Kadish, C. J. Chang, P. Palan, J. Basu, R. Tachezy, R. Lewis, and S. Romney. 1995. Persistent genital human papillomavirus infection as a risk factor for persistent cervical dysplasia. J. Natl. Cancer Inst. 87: 1365-1371.
8. Howley, P. M. 1996. *Papillomavirinae*: The viruses and their replication, p. 2045-2076. In B. N. Fields, and D. M. Knipe (eds), Fields Virology, Third Edition, Second ed. Raven Press, New York.
9. Kloster, B. E., D. A. Manias, R. S. Ostrow, M. K. Shaver, S. W. McPherson, S. R. Rangen, H. Uno, and A. J. Faras. 1988. Molecular cloning and characterization of the DNA of two papillomaviruses from monkeys. Virology. 166: 30-40.
10. Lancaster, W. D., and C. Olson. 1982. Animal papillomaviruses. Microbiological Reviews. 46: 191-207.
11. Ostrow, R. S., K. V. LaBresh, and A. J. Faras. 1991. Characterization of the complete RhPV1 genomic sequence and an integration locus from a metastatic tumor. Virology. 181: 424-429.
12. Ostrow, R. S., R. C. McGlennen, M. K. Shaver, B. E. Kloster, D. Houser, and A. J. Faras. 1990. A rhesus monkey model for sexual transmission of a papillomavirus isolated from a squamous cell carcinoma. Proceedings of the National Academy of Sciences United States of America. 87: 8170-8174.
13. Parkin, D. M., P. Pisani, and J. Ferlay. 1993. Estimates of the worldwide incidence of eighteen major cancers in 1985. Int. J. Cancer. 54: 594-606.
14. Pfister, H. 1984. Biology and biochemistry of papillomaviruses. Rev. Physiol. Biochem. Pharmacol. 99:111-181.
15. Rowson, K. E. K., and B. W. J. Mahy. 1967. Human papova (wart) virus. Bacteriological Reviews. 31: 110-131.
16. zur Hausen, H. 1989. Papillomaviruses in anogenital cancer as a model to understand the role of viruses in human cancers. Cancer Res. 49: 4677-4681.
17. Hummel Fields, and D. M. Knipe (eds), Fields Virology, Third Edition, Second ed. Raven Press, New York.
18. Hummel, M., J. B. Hudson, and L. A. Laimins (1992) Differentiation-induced and constitutive transcription of human papillomavirus type 31b in cell lines containing viral episomes. J. Virol. 66: 6070-6080.
19. Ozbun, M. A., and C. Meyers (1998) Temporal usage of multiple promoters during the life cycle of human papillomavirus type 31b. J. Virol. 72: 2715-2722.
20. Ozbun, M. A., and C. Meyers (1999) Two novel promoters in the upstream regulatory region of human papillomavirus type 31b are negatively regulated by epithelial differentiation. J. Virol. 73: 3505-3510.

I claim:

1. A method for modeling human papillomavirus infection in a Rhesus macaque, said method comprising the step of:
a) contacting Rhesus macaque anogenital and/or cervical tissue or respiratory epithelial tissue with infectious Rhesus papillomavirus (RhPV) virions, whereby infection of anogenital and/or cervical or respiratory epithelial tissue occurs with said virus; and
b) observing development of symptoms and/or viral replication in said tissue.

2. The method of claim 1 wherein said Rhesus papillomavirus is RhPV1.

3. The method of claim 1, further comprising the steps of administering a test composition to the Rhesus monkey with which the infectious Rhesus papillomavirus virus has been contacted and performing a physical observation of the monkey over a three to five year time to observe whether no infection results or whether infection is delayed or whether infection is less severe than in a comparison animal to which no test composition has been administered, whereby the test composition is identified as an inhibitor of infection when no infection results or when infection is delayed or when infection is diminished.

4. The method of claim 3, wherein the physical observation is a Pap smear, an anogenital swab, colposcopy, or polymerase chain reaction to confirm papillomavirus DNA in a sample from said monkey.

* * * * *

UNITED STATES PATENT AND TRADEMARK OFFICE
CERTIFICATE OF CORRECTION

PATENT NO. : 7,285,386 B2
APPLICATION NO. : 10/978239
DATED : October 23, 2007
INVENTOR(S) : Michelle A. Ozbun Page 1 of 1

It is certified that error appears in the above-identified patent and that said Letters Patent is hereby corrected as shown below:

Column 1, line 15, cancel the text beginning with "The United States Government" to and ending "Health and Human Services." in column 1, line 21, and insert the following text:

--This invention was made with government support under Contract Nos. CA085747 and CA103645 awarded by the National Cancer Institute of the National Institutes of Health. The government has certain rights in the invention.--

Signed and Sealed this

Twenty-fourth Day of March, 2009

JOHN DOLL
*Acting Director of the United States Patent and Trademark Office*